United States Patent
Bhatnagar et al.

(10) Patent No.: US 9,445,845 B2
(45) Date of Patent: *Sep. 20, 2016

(54) DYNAMIC STABILIZATION SYSTEMS AND DEVICES FOR A SPINE

(71) Applicant: JMEA Corporation, Rockville, MD (US)

(72) Inventors: Mohit K. Bhatnagar, Potomac, MD (US); James A. Sack, Elverson, PA (US); Jack Y. Yeh, North Potomac, MD (US)

(73) Assignee: JMEA Corporation, Rockville, MD (US)

( * ) Notice: Subject to any disclaimer, the term of this patent is extended or adjusted under 35 U.S.C. 154(b) by 200 days.

This patent is subject to a terminal disclaimer.

(21) Appl. No.: 13/849,788

(22) Filed: Mar. 25, 2013

(65) Prior Publication Data

US 2013/0282063 A1    Oct. 24, 2013

Related U.S. Application Data

(63) Continuation of application No. 12/770,082, filed on Apr. 29, 2010, now Pat. No. 8,425,568, which is a continuation of application No. 11/840,731, filed on Aug. 17, 2007, now Pat. No. 8,080,038.

(51) Int. Cl.
*A61B 17/70* (2006.01)

(52) U.S. Cl.
CPC ....... *A61B 17/7028* (2013.01); *A61B 17/7004* (2013.01); *A61B 17/7032* (2013.01); *A61B 17/702* (2013.01); *A61B 17/7005* (2013.01); *A61B 17/7007* (2013.01);

(Continued)

(58) Field of Classification Search
CPC .......... A61B 17/7005; A61B 17/7007; A61B 17/7008; A61B 17/7019; A61B 17/702; A61B 17/7026; A61B 17/7028; A61B 17/7029; A61B 17/7031

See application file for complete search history.

(56) References Cited

U.S. PATENT DOCUMENTS 575,451 A * 1/1897 Yost .............................. 267/73
3,507,069 A * 4/1970 Borba, Sr. .................. 43/18.1 R (Continued)

FOREIGN PATENT DOCUMENTS

| FR | 2709245 | 3/1995 |
|----|---------|--------|
| FR | 2717370 | 9/1995 |

(Continued)

OTHER PUBLICATIONS

International Preliminary Report on Patentability and Written Opinion mailed Mar. 4, 2010 from PCT Application No. PCT/US2008/072114.

(Continued)

*Primary Examiner* — Ellen C Hammond
(74) *Attorney, Agent, or Firm* — Plumsea Law Group, LLC

(57) ABSTRACT

A dynamic stabilization device is disclosed. The device includes a dual spring member comprising an outer spring and an inner spring that have approximately equal working lengths. The dynamic stabilization device is also configured so that the dual spring member does not undergo stresses greater than an effective fatigue limit that is related to a fatigue limit of the spring. Methods for treating a deformity of a spine using a dynamic stabilization device are also disclosed.

20 Claims, 17 Drawing Sheets

(52) U.S. Cl.
CPC ....... *A61B 17/7008* (2013.01); *A61B 17/7019* (2013.01); *A61B 17/7026* (2013.01); *A61B 17/7029* (2013.01); *A61B 17/7031* (2013.01)

(56) References Cited

U.S. PATENT DOCUMENTS

| | | | |
|---|---|---|---|
| 3,511,280 A | | 5/1970 | Mercier |
| 3,807,394 A | * | 4/1974 | Attenborough ................ 606/60 |
| 3,862,751 A | | 1/1975 | Schwaller |
| 4,817,927 A | | 4/1989 | Martin |
| 4,854,304 A | | 8/1989 | Zielke |
| 4,988,349 A | | 1/1991 | Pennig |
| 5,034,011 A | | 7/1991 | Howland |
| 5,101,213 A | | 3/1992 | Harada et al. |
| 5,129,388 A | | 7/1992 | Vignaud et al. |
| 5,176,679 A | | 1/1993 | Lin |
| 5,180,393 A | | 1/1993 | Commarmond |
| 5,330,473 A | | 7/1994 | Howland |
| 5,382,248 A | | 1/1995 | Jacobson et al. |
| 5,385,583 A | | 1/1995 | Cotrel |
| 5,423,816 A | * | 6/1995 | Lin ................................ 606/247 |
| 5,562,663 A | | 10/1996 | Wisnewski et al. |
| 5,662,651 A | | 9/1997 | Tornier et al. |
| 5,672,175 A | | 9/1997 | Martin |
| 5,704,937 A | | 1/1998 | Martin |
| 5,713,898 A | | 2/1998 | Stucker et al. |
| 5,716,356 A | | 2/1998 | Biedermann et al. |
| 5,733,284 A | | 3/1998 | Martin |
| 5,961,517 A | * | 10/1999 | Biedermann et al. ...... 606/86 A |
| 6,077,262 A | | 6/2000 | Schlapfer et al. |
| 6,402,750 B1 | | 6/2002 | Atkinson et al. |
| 6,458,132 B2 | | 10/2002 | Choi |
| 6,485,492 B1 | | 11/2002 | Halm et al. |
| 6,585,738 B1 | | 7/2003 | Mangione et al. |
| 6,616,668 B2 | | 9/2003 | Altarac et al. |
| 6,966,910 B2 | | 11/2005 | Ritland |
| 6,986,771 B2 | | 1/2006 | Paul et al. |
| 6,989,011 B2 | | 1/2006 | Paul et al. |
| 7,029,475 B2 | | 4/2006 | Panjabi |
| 7,329,258 B2 | | 2/2008 | Studer |
| 7,651,515 B2 | | 1/2010 | Mack et al. |
| 7,699,875 B2 | | 4/2010 | Timm |
| 7,713,288 B2 | | 5/2010 | Timm et al. |
| 7,722,649 B2 | | 5/2010 | Biedermann et al. |
| 8,080,038 B2 | | 12/2011 | Bhatnagar et al. |
| 8,709,090 B2 | * | 4/2014 | Makower et al. ......... 623/20.21 |
| 2002/0095154 A1 | | 7/2002 | Atkinson et al. |
| 2002/0116001 A1 | | 8/2002 | Schafer et al. |
| 2003/0109880 A1 | | 6/2003 | Shirado et al. |
| 2003/0220643 A1 | | 11/2003 | Ferree |
| 2004/0049190 A1 | | 3/2004 | Biedermann et al. |
| 2004/0236327 A1 | | 11/2004 | Paul et al. |
| 2004/0236328 A1 | | 11/2004 | Paul et al. |
| 2004/0236329 A1 | | 11/2004 | Panjabi |
| 2004/0243127 A1 | | 12/2004 | Vincent-Prestigiacomo |
| 2004/0267260 A1 | | 12/2004 | Mack et al. |
| 2005/0043732 A1 | | 2/2005 | Dalton |
| 2005/0065514 A1 | * | 3/2005 | Studer ............................. 606/61 |
| 2005/0085814 A1 | | 4/2005 | Sherman et al. |
| 2005/0085815 A1 | | 4/2005 | Harms et al. |
| 2005/0131405 A1 | | 6/2005 | Molz, IV et al. |
| 2005/0171543 A1 | | 8/2005 | Timm et al. |
| 2005/0177156 A1 | | 8/2005 | Timm et al. |
| 2005/0182400 A1 | | 8/2005 | White |
| 2005/0182409 A1 | | 8/2005 | Callahan et al. |
| 2005/0203513 A1 | | 9/2005 | Jahng et al. |
| 2005/0203514 A1 | | 9/2005 | Jahng et al. |
| 2005/0203519 A1 | | 9/2005 | Harms et al. |
| 2005/0222569 A1 | | 10/2005 | Panjabi |
| 2005/0245930 A1 | | 11/2005 | Timm et al. |
| 2005/0288670 A1 | | 12/2005 | Panjabi et al. |
| 2005/0288672 A1 | | 12/2005 | Ferree |
| 2006/0015100 A1 | | 1/2006 | Panjabi et al. |
| 2006/0036240 A1 | * | 2/2006 | Colleran et al. ................ 606/61 |
| 2006/0041259 A1 | | 2/2006 | Paul et al. |
| 2006/0064090 A1 | * | 3/2006 | Park ................................ 606/61 |
| 2006/0106381 A1 | | 5/2006 | Ferree et al. |
| 2006/0129147 A1 | | 6/2006 | Biedermann et al. |
| 2006/0142758 A1 | | 6/2006 | Petit |
| 2006/0142760 A1 | | 6/2006 | McDonnell |
| 2006/0184171 A1 | | 8/2006 | Biedermann et al. |
| 2006/0212033 A1 | | 9/2006 | Rothman et al. |
| 2006/0229608 A1 | | 10/2006 | Foster et al. |
| 2006/0229612 A1 | * | 10/2006 | Rothman et al. ............... 606/61 |
| 2006/0229613 A1 | | 10/2006 | Timm et al. |
| 2006/0247632 A1 | | 11/2006 | Winslow et al. |
| 2006/0247637 A1 | | 11/2006 | Colleran et al. |
| 2006/0282080 A1 | | 12/2006 | Albert et al. |
| 2006/0293657 A1 | | 12/2006 | Hartmann |
| 2007/0016193 A1 | | 1/2007 | Ritland |
| 2007/0032123 A1 | * | 2/2007 | Timm et al. ................... 439/395 |
| 2007/0043356 A1 | | 2/2007 | Timm et al. |
| 2007/0049936 A1 | * | 3/2007 | Colleran et al. ................ 606/61 |
| 2007/0049937 A1 | | 3/2007 | Matthis et al. |
| 2007/0055244 A1 | | 3/2007 | Jackson |
| 2007/0055247 A1 | | 3/2007 | Jahng |
| 2007/0233086 A1 | * | 10/2007 | Harms et al. ................... 606/61 |
| 2009/0048631 A1 | | 2/2009 | Bhatnagar et al. |
| 2009/0105760 A1 | | 4/2009 | Frey |
| 2010/0211104 A1 | | 8/2010 | Moumene et al. |
| 2010/0228298 A1 | | 9/2010 | Bhatnagar et al. |

FOREIGN PATENT DOCUMENTS

| | | |
|---|---|---|
| FR | 2799949 | 4/2001 |
| GB | 2382304 | 5/2003 |
| WO | 03047442 | 6/2003 |
| WO | 2006002359 | 1/2006 |

OTHER PUBLICATIONS

Extended European Search Report and Opinion, mailed Apr. 2, 2013, from European Application No. 08797121.4.

European Patent Office Communication under Rule 71(3) EPC (Intention to Grant), dated Dec. 17, 2015, from European Application No. 08797121.4.

Response to Extended European Search Report and Opinion, filed Oct. 22, 2013 in European Patent Application No. 08797121.4.

Office Action dated Mar. 18, 2015 in European Patent Application No. 08797121.4.

Response to Office Action, filed Sep. 18, 2015 in European Patent Application No. 08797121.4.

* cited by examiner

DYNAMIC STABILIZATION SYSTEMS AND DEVICES FOR A SPINE

CROSS REFERENCE TO RELATED APPLICATIONS

This application is a continuation of U.S. patent application Ser. No. 12/770,082, filed Apr. 29, 2010, now U.S. Pat. No. 8,425,568, issued Apr. 23, 2013, which is a continuation of U.S. patent application Ser. No. 11/840,731, filed Aug. 17, 2007, now U.S. Pat. No. 8,080,038, issued Dec. 20, 2011, both of which are herein incorporated by reference in their entirety.

BACKGROUND OF THE INVENTION

1. Field of the Invention

The present invention relates generally to spinal implantations and in particular to a dynamic stabilization device configured for the spine.

2. Description of Related Art

Methods of spinal stabilization have previously been proposed. Previous methods have incorporated various components configured to provide some type of flexibility. Jahng et al. (U.S. patent number 2005/0203513) teaches a spinal stabilization device. The stabilization device includes a longitudinal member having first and second ends as well as a flexible section disposed between the first and second ends. Jahng further teaches a cross sectional profile for the flexible section that is different than the cross sectional profiles of the first and second ends. Jahng teaches a flexible section that includes spiral cut grooves to improve flexibility.

Generally, spiral cut grooves may not provide the same degree of flexibility and support as a spring. Methods of spinal stabilization including screws have also been proposed. Timm et al. (U.S. patent number 2005/0171543) is directed to a system for effecting multi-level spine stabilization. Timm teaches a system including a plurality of pedicle screws that are joined by rods. Timm further teaches that at least one of the rods includes a dynamic stabilizing member. Timm teaches an inner first spring and an outer second spring. In the Timm design, the inner first spring is generally disposed within the outer second spring. Timm teaches springs that are not connected directly to the stabilization device at their ends, but instead are free springs disposed between two surfaces.

Colleran et al. (U.S. patent number 2006/0036240), teaches a system and method for dynamic skeletal stabilization. Colleran teaches two screws that are each associated with a separate bracing portion. Colleran teaches a spring and two stops that allow the two bracing portions to move longitudinally with respect to one another. This provides some degree of movement between the two screws. In the Colleran design, one of the brace portions may also bend.

Rothman et al. (U.S. patent number 2006/0229612) teaches a method for vertebral stabilization using sleeved springs. Rothman teaches a spring that is disposed between two anchoring elements. Rothman further teaches sleeve elements that cover the ends of the springs. The sleeve elements include an inner surface configured to receive the springs and an outer surface configured to engage the anchoring elements. The sleeve elements include ends that serve as stops for the spring.

These methods and systems incorporating springs as dynamic components have several drawbacks. First, the methods and systems taught here lack well defined connection points for the springs, and instead rely on stops or sleeve assisted stops. Also, in these systems, the springs may not facilitate inward tension as the springs are stretched, nor facilitate outward tension that is associated with spring compression.

Methods of attaching rods to bone screws have been previously proposed. Tornier et al. (U.S. Pat. No. 5,662,651) teaches an external or internal fixator for repairing fractures of arthroplasties of the skeleton. Tornier teaches an implant screw that is connected to a support that is angularly indexed with respect to the screw. The support includes a cavity configured to receive a connecting rod. Tornier further teaches a locking screw that is fastened into place into the support member, thereby locking the connecting rod into place. The Tornier design has several drawbacks. The connecting rod is attached to a support that is separate from the screw, providing a potentially weakened connection between the connecting rod and the screw. Additionally, the locking screw does not include provisions to easily receive the surface of the connecting rod. Furthermore, Tornier does not teach a drive receiving surface used to install the screw.

There is a need in the art for a design that solves many of the problems of the prior art.

SUMMARY OF THE INVENTION

A dynamic stabilization device configured for the spine is disclosed. In one aspect, the invention provides a dynamic stabilization device configured for implantation into a spine, comprising: an outer spring and an inner spring, wherein the inner spring is disposed within the outer spring; and where the outer spring has a first working length that is equal to a second working length of the inner spring.

In another aspect, the inner spring is configured to attach to a first threaded portion of a first rod of the dynamic stabilization device.

In another aspect, the outer spring is configured to attach to a second threaded portion of a second rod of the stabilization device.

In another aspect, the first rod is attached to a first anchor configured for implantation into a first vertebra.

In another aspect, the second rod is attached to a second anchor configured for implantation into a second vertebra.

In another aspect, the invention provides a dynamic stabilization device configured for implantation into a spine, comprising: a dual spring member including a first end; a first rod including a first threaded portion; and where the first end of the dual spring member is configured to mechanically attach to the first threaded portion of the first rod.

In another aspect, a second end of the dual spring member is configured to attach to a second threaded portion associated with a second rod.

In another aspect, the dual spring member comprises an outer spring and an inner spring.

In another aspect, the outer spring is configured to connect to a first outer threaded portion of the first rod.

In another aspect, the inner spring is configured to connect to a first inner threaded portion of the first rod.

In another aspect, the inner spring and the outer spring are connected at the second end of the dual spring member.

In another aspect, the inner spring and the outer spring have approximately equal working lengths.

In another aspect, the inner spring and the outer spring are configured to experience stresses that are less than a fatigue limit associated with the inner spring and the outer spring.

In another aspect, the invention provides a dynamic stabilization device configured for implantation into a spine, comprising: a dual spring member including an outer spring and an inner spring, the dual spring member having a fatigue limit; and where the dynamic stabilization device is configured so that stresses applied to the dual spring member are always below an effective fatigue limit.

In another aspect, the fatigue limit is associated with a stress selected from a group consisting essentially of shear stresses, tensions stresses, compression stresses, torsional stresses, rotational stresses, and any combination thereof.

In another aspect, the effective fatigue limit is between 10 percent of the fatigue limit and 75 percent of the fatigue limit.

In another aspect, the dual spring member has a life expectancy that is effectively indefinite.

In another aspect, the dual spring member is connected to a first outer threaded portion at a first end.

In another aspect, the dual spring member comprises an outer spring and an inner spring.

In another aspect, the outer spring has a first working length that is approximately equal to a second working length associated with the inner spring.

In another aspect, the inner spring comprises an inner coil and wherein the outer spring comprises an outer coil, and wherein the inner coil is different than the outer coil.

In another aspect, the inner spring has a first shape and wherein the outer spring has a second shape, and wherein the first shape is different than the second shape.

In another aspect, the invention provides a dynamic stabilization device configured for implantation into a spine, comprising: an anchor configured for implantation into a bone, including a proximal portion and a distal portion; the proximal portion including threading configured to penetrate a vertebra; the distal portion including a drive receiving surface; the distal portion including a first set of recesses configured to receive ridges associated with a rod; and where the first set of recesses is disposed within a drive receiving surface and wherein a cap configured to cover the distal portion includes a second set of recesses configured to receive the ridges.

In another aspect, the rod is associated with a dual spring member.

In another aspect, the dual spring member includes an inner spring and an outer spring;

In another aspect, the inner spring and the outer spring have approximately equal working lengths.

In another aspect, the dual spring member is configured to attach to a threaded portion of the rod.

In another aspect, the maximum stress applied to the dual spring member is below an effective fatigue limit that is less than half of a fatigue limit.

In another aspect, the inner spring and the outer spring are continuously formed at a first end of the dual spring member and at a second end of the dual spring member.

In another aspect, the inner spring and the outer spring are physically separated at a first end of the dual spring member and at a second end of the dual spring member.

In another aspect, the inner spring and the outer spring are continuously formed at a first end of the dual spring member and wherein the inner spring and the outer spring are physically separated at a second end of the dual spring member.

In another aspect, a surface of the rod is textured.

In another aspect, the ridges have a shape selected from the group consisting essentially of sinusoidal ridges, box-like ridges, triangular ridges, rounded ridges, and any combination thereof.

In another aspect, the dynamic stabilization device may be used to dynamically treat or correct various deformities.

In another aspect, the anchor is a screw.

In another aspect, the anchor is a hook.

In another aspect, the rod includes threading.

In another aspect, the rod includes a locking member configured to engage at least one spring.

In another aspect, the invention provides a dynamic stabilization system configured for implantation into a spine, comprising: a first dynamic stabilization device configured to be attached to adjacent vertebrae, the first dynamic stabilization device being pre-stressed and including a first residual stress; a second dynamic stabilization device configured to be attached to the adjacent vertebrae, the second dynamic stabilization device being pre-stressed and including a second residual stress; and wherein the first and second dynamic stabilization devices are configured to apply a force to the adjacent vertebrae thereby adjusting the relative positions of the adjacent vertebrae.

In another aspect, wherein the first residual stress is different than the second residual stress.

In another aspect, wherein the first residual stress is tension and the second residual stress is compression, and wherein a rotational force is applied to the adjacent vertebrae whereby scoliosis may be treated.

In another aspect, wherein the first residual stress is substantially equal to the second residual stress, and wherein a translational force is applied to the adjacent vertebrae whereby spondylolisthesis may be treated.

In another aspect, wherein the first residual stress is substantially equal to the second residual stress, and wherein a flexion force is applied to the adjacent vertebrae whereby spinal stenosis may be treated.

Other systems, methods, features, and advantages of the invention will be, or will become apparent to one with skill in the art upon examination of the following figures and detailed description. It is intended that all such additional systems, methods, features, and advantages be included within this description, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

DETAILED DESCRIPTION OF THE PREFERRED EMBODIMENTS

Figure 1:
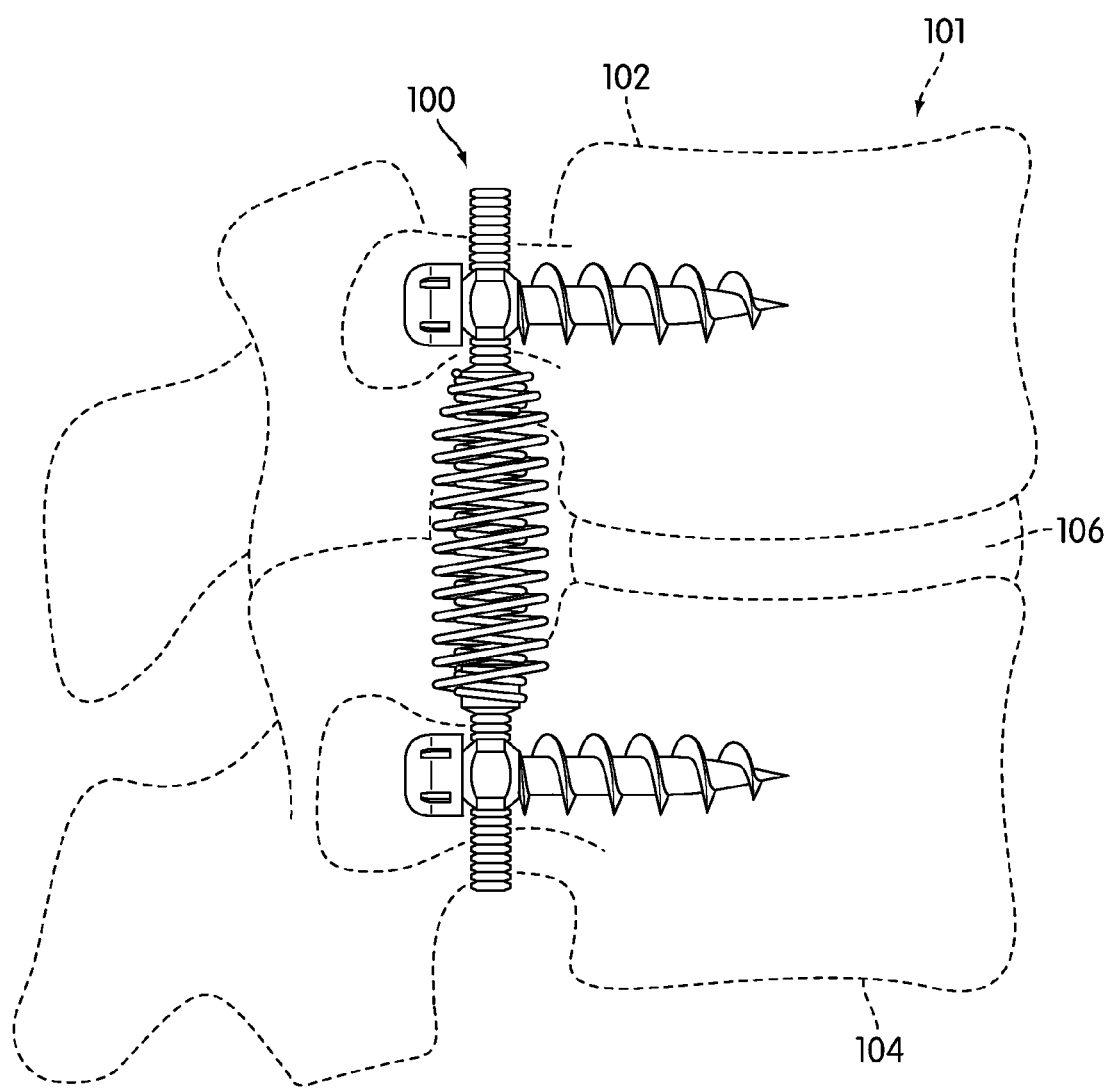
FIG. 1 is a side view of a preferred embodiment of a spine with a dynamic stabilization device.

FIG. 1 is a side view of a preferred embodiment of dynamic stabilization device 100. In this embodiment, dynamic stabilization device 100 is configured to attach to spine 101. Generally, dynamic stabilization device 100 may be applied in surgeries intended to address disc degenerative diseases, spinal stenosis, spondylolisthesis, scoliosis, as well as other spinal problems. Dynamic stabilization device 100 may allow for dynamic support to spine 101 to provide immediate postoperative stability when used in the case of disc replacement or nucleus replacement.

In this embodiment, dynamic stabilization device 100 is configured to attach to first vertebra 102 and second vertebra 104. First vertebra 102 and second vertebra 104 are further associated with spinal disc 106. Spinal disc 106 is disposed between vertebrae 102 and 104. In some embodiments, spinal disc 106 could be surgically altered, including reduction in size. In other embodiments, spinal disc 106 may be a disc implant or disc replacement configured to provide support between vertebrae 102 and 104 following the removal of a spinal disc.

Figure 2:
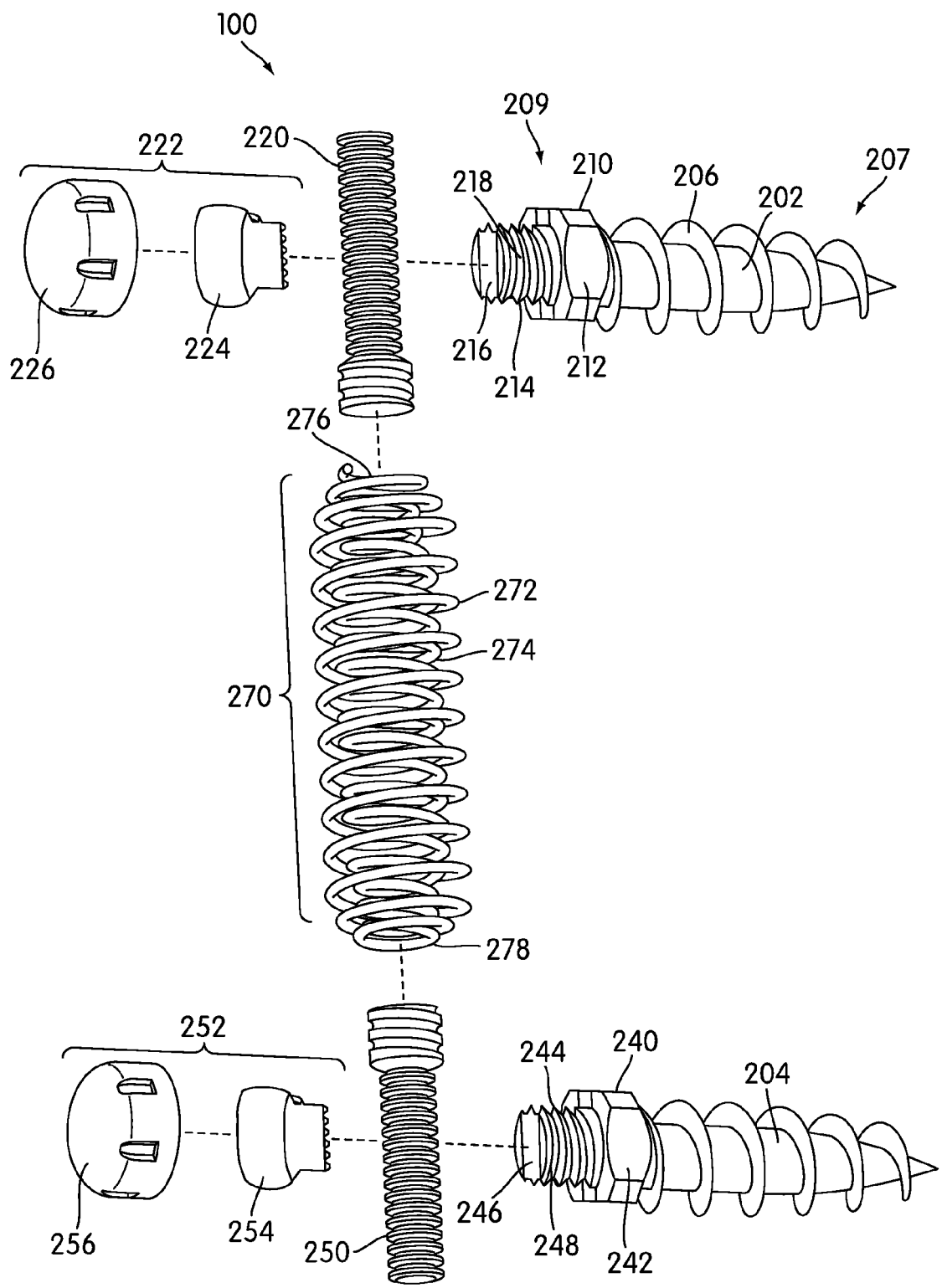
FIG. 2 is an exploded isometric view of a preferred embodiment of a dynamic stabilization device.
Figure 3:
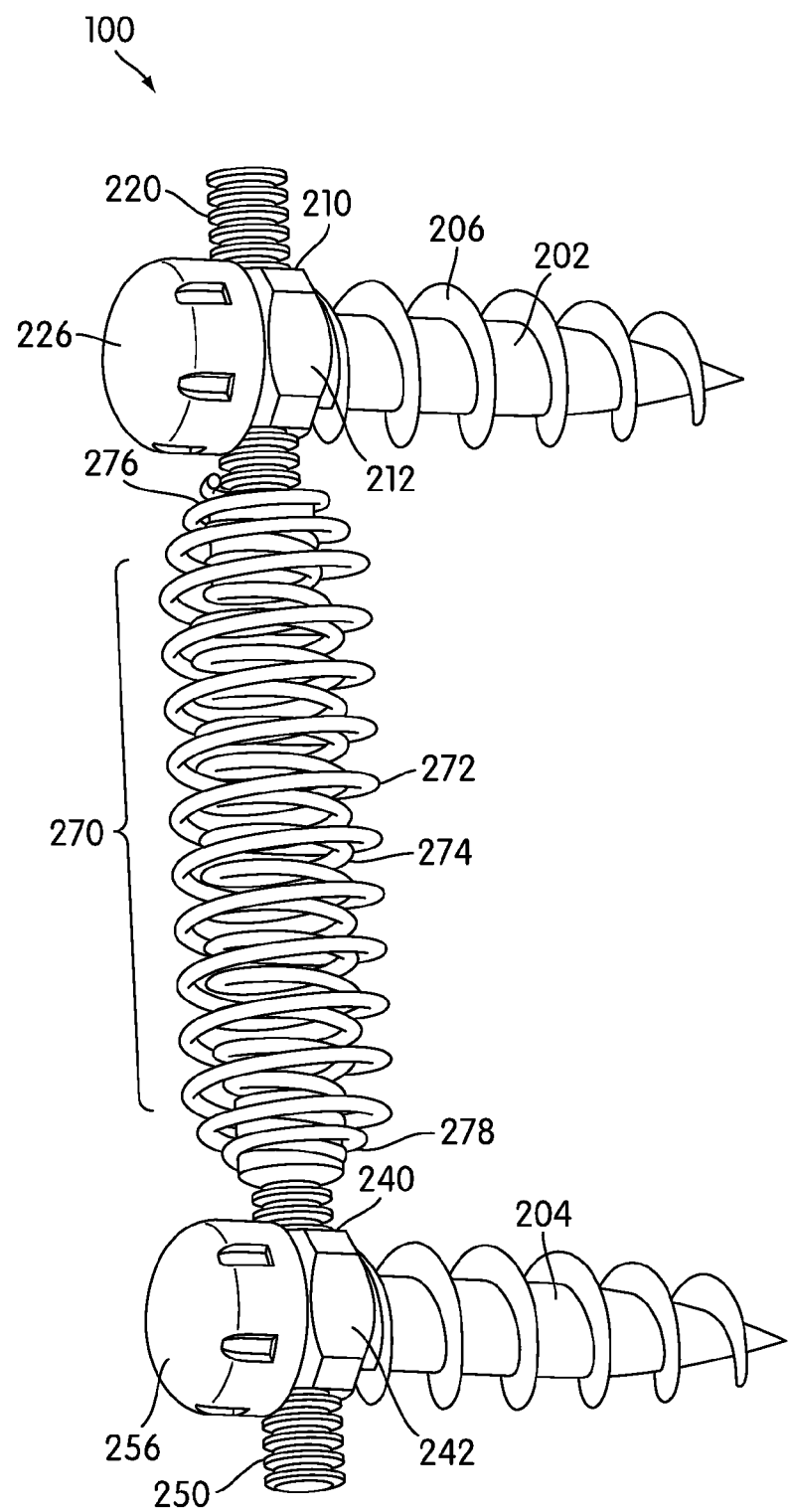
FIG. 3 is an isometric view of a preferred embodiment of a dynamic stabilization device.

FIGS. 2 and 3 are intended to illustrate the various components associated with dynamic stabilization device 100 in a preferred embodiment. Preferably, dynamic stabilization device 100 includes first anchor 202 and second anchor 204. In some embodiments, anchors 202 and 204 are bone screws. In other embodiments, anchors 202 and 204 may be pedicle screws that may be configured to implant or screw into pedicles of vertebrae.

First anchor 202 and second anchor 204 preferably include threading 206 disposed on distal portion 207 of anchors 202 and 204. Preferably, threading 206 may have a major diameter that is sufficiently large compared to the minor diameter of threading 206. Furthermore, the pitch of threading 206 is preferably large enough to provide adequate holding strength. Using this preferred threading arrangement may provide increased strength of the connection between anchors 202 and 204 and vertebrae 102 and 104, respectively.

First anchor 202 preferably includes first drive receiving surface 210 disposed at proximal portion 209. Preferably, first drive receiving surface 210 is disposed circumferentially around first anchor 202. In other embodiments, the drive receiving surface is disposed within anchor head 214. In the preferred embodiment, first drive receiving surface 210 may be a hexagonal surface configured to receive a wrench or ratchet of some kind. First drive receiving surface 210 may include first flat side 212. Preferably, one or more additional flat sides (not shown) are adjacent to first flat side 212 on first drive receiving surface 210. Using this arrangement, a wrench, socket or other tool may be applied to first flat side 212 and one or more additional flat sides (not shown) to manipulate first anchor 202. In particular, with this arrangement, first anchor 202 may be drilled or otherwise screwed into place with respect to first vertebra 102.

In other embodiments, first drive receiving surface 210 may have a different shape. Furthermore, in some embodiments, additional provisions may be provided for driving first anchor 202 into place. In some embodiments, first anchor 202 may include a drive such as are found in the heads of various types of screws for receiving a screwdriver including, but not limited to: slotted drives, Phillips drives, Torx drives, Hex drives, and Robertson drives.

First anchor 202 may also include first anchor head 214. Preferably, first anchor 202 is attached to first drive receiving surface 210. First anchor head 214 may include first slotted portion 216. Additionally, first anchor head 214 may include first anchor threading 218.

Preferably, first anchor 202 may be associated with first rod 220. In some embodiments, first anchor portion 202 may be configured to receive first rod 220 at first slotted portion 216 of first anchor head 214. Preferably, first slotted portion 216 is wide enough and deep enough to receive first rod 220. In an alternative embodiment, first slotted portion 216 and first rod 220 may be joined using an interference fit. In this case, first slotted portion 216 may be just large enough so that first rod 220 can be wedged into first slotted portion 216.

Furthermore, first anchor 202 may be associated with first cap 222. First cap 222 preferably includes first inner cap 224 and first outer cap 226. Preferably, first inner cap 224 is configured to fit within first outer cap 226. In some embodiments, first inner cap 224 may be formed integrally with first outer cap 226 resulting in a one piece or monolithic single cap. Furthermore, first inner cap 224 is preferably configured to receive first rod 220, while first outer cap 226 is configured to engage first anchor head 214. An assembled view of first cap 222, first rod 220 and first anchor 202 can be seen in FIG. 3. Details of this assembly will be explained later in this detailed description.

Preferably, second anchor 204 is substantially similar to first anchor 202. In particular, second anchor 204 may include second drive receiving surface 240, including second flat side 242. Furthermore, second anchor 204 may include second anchor head 244. Second anchor head 244 may be associated with second slotted portion 246 and second anchor threading 248.

Preferably, second anchor 204 may be associated with second rod 250. In some embodiments, second anchor 204 may be configured to receive second rod 250 at second slotted portion 246 of second anchor head 244. Preferably, second slotted portion 246 is wide enough and deep enough to receive second rod 250. In an alternative embodiment, second slotted portion 256 and second rod 250 may be joined using an interference fit. In this case, second slotted portion 256 may be just large enough so that second rod 250 can be wedged into second slotted portion 256.

Furthermore, second anchor 204 may be associated with second cap 252. Second cap 252 preferably includes second inner cap 254 and second outer cap 256. Preferably, second inner cap 254 is configured to fit within second outer cap 256. In some embodiments, second inner cap 254 may be formed integrally with second outer cap 256 resulting in a one piece or monolithic single cap. Furthermore, second inner cap 254 is preferably configured to receive second rod 250, while second outer cap 256 is configured to engage second anchor head 244. An assembled view of second cap 252, second rod 250 and second anchor 204 can be seen in FIG. 3. Details of this assembly will be explained later in this detailed description.

Preferably, dynamic stabilization device 100 is further associated with dual spring member 270. In some embodiments, dual spring member 270 comprises outer spring 272 and inner spring 274. Dual spring member 270 preferably includes first end 276 and second end 278. First end 276 may be configured to attach to first rod 220 and second end 278 may be configured to attach to second rod 250. As seen in FIG. 3, dual spring member 270 facilitates attachment between first anchor 202 and second anchor 204, generally creating some interdependence between anchors 202 and 204.

In an alternative embodiment, other types of anchors may be used with the dynamic stabilization device. In some cases, other types of fasteners known in the art other than bone screws may be used to attach the dynamic stabilization device to the adjacent vertebrae. In a preferred embodiment, one or more hooks may be used as anchors to minimize the trauma to the adjacent vertebrae during the fastening process. In other embodiments, plates attached to the vertebral body may be used as an alternative anchor.

Figure 4:
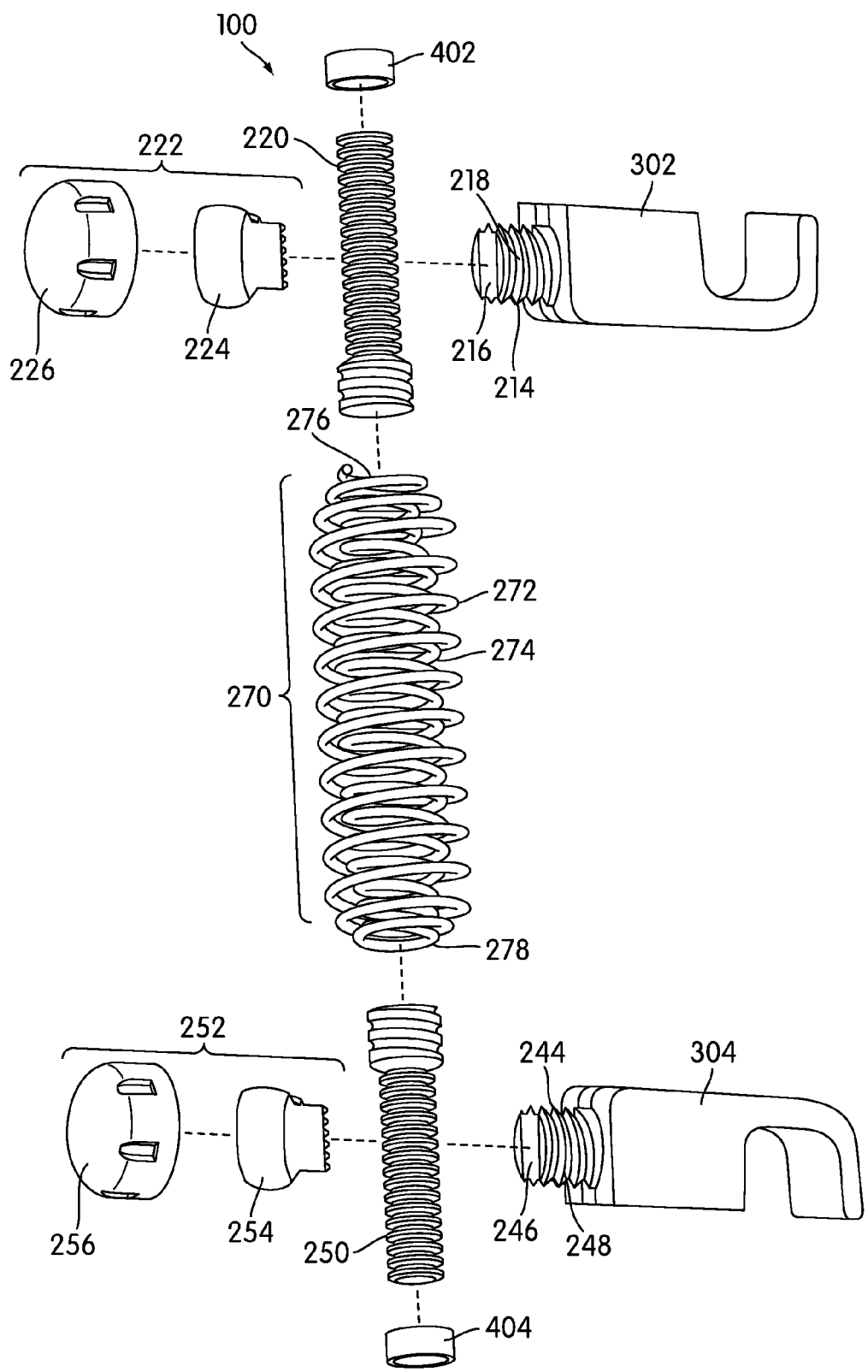
FIG. 4 is an exploded isometric view of an alternative embodiment of a dynamic stabilization device.
Figure 5:
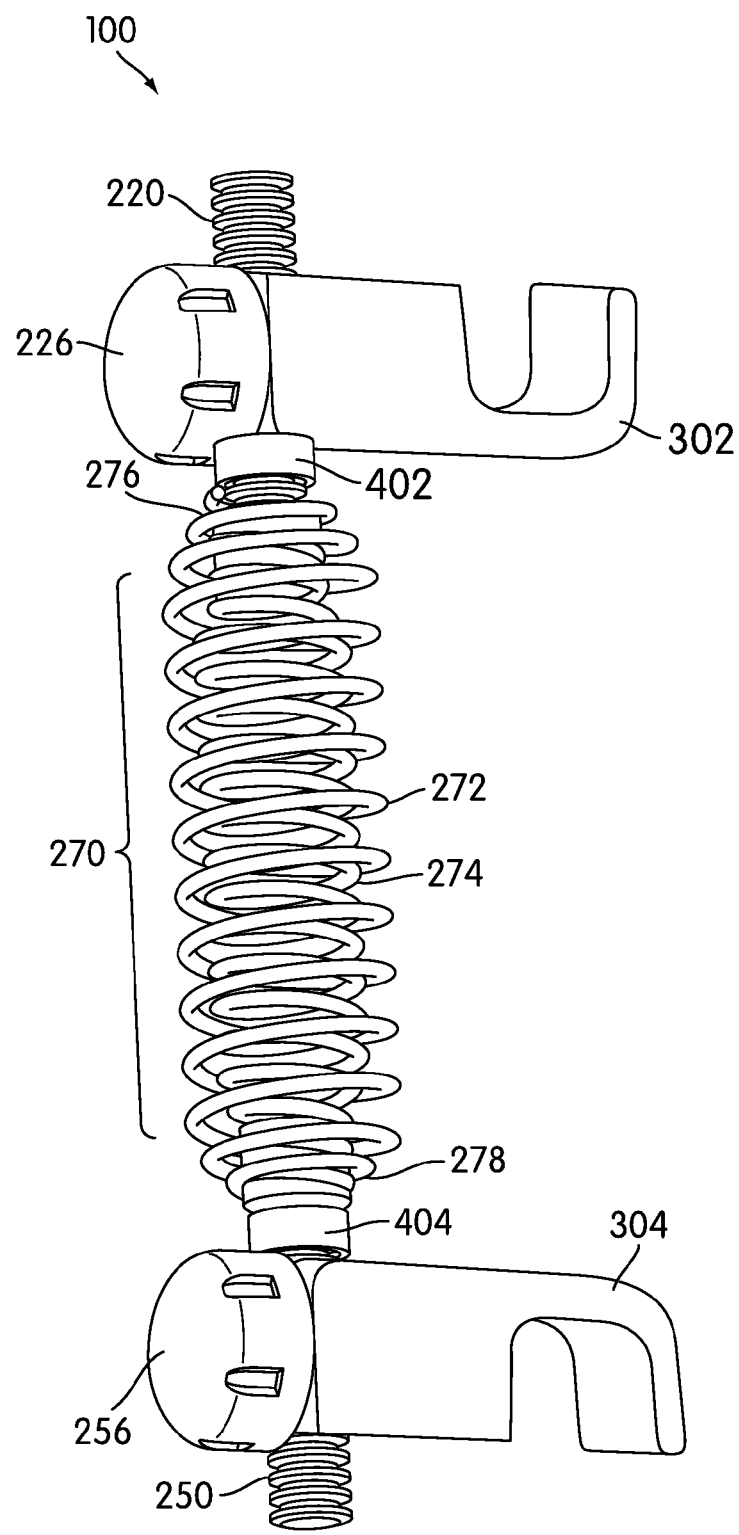
FIG. 5 is an isometric view of an alternative embodiment of a dynamic stabilization device.

FIGS. 4 and 5 are intended to illustrate an alternative embodiment of dynamic stabilization device 100. Many of the components discussed with respect to FIGS. 2 and 3 are identical for the current embodiment. In this embodiment, however, dynamic stabilization device 100 includes first hook 302 and second hook 304. In this preferred embodiment, first hook 302 and second hook 304 may be configured to connect to the transverse processes, lamina or spinous processes of adjacent vertebrae.

In some embodiments, a dynamic stabilization device may include provisions for locking a dual spring member into place. In some cases, this may be accomplished by including locking members. In a preferred embodiment, the locking members may be configured to limit the motion of the ends of the dual spring member.

Referring to FIG. 4, dynamic stabilization device 100 may include first locking member 402 and second locking member 404. In some embodiments, locking members 402 and 404 may be caps that are configured to slide over rods 220 and 250, respectively. In some cases, locking members 402 and 404 may include provisions for locking or snapping into place over rods 220 and 250, respectively. In some embodiments, locking members 402 and 404 may also be screwed onto rods 220 and 250 respectively.

Referring to FIG. 5, first locking member 402 may be disposed between first hook 302 and first end 276 of dual spring member 270. This preferred arrangement may prevent first end 276 of dual spring member 270 from moving with respect to first rod 220. In particular, first locking member 402 may prevent outer spring 272 from moving at first end 276. In some embodiments, second locking member 404 is disposed between second hook 304 and second end 278 of dual spring member 270. This arrangement preferably prevents second end 278 from moving in a manner similar to the way that first locking member 402 prevents movement at first end 276.

It should be understood that locking members could be used in other embodiments of a dynamic stabilization device. Although the current embodiment includes locking members used with hooks, in other embodiments, locking members could be used with any type of anchors for a dynamic stabilization device, including plates. Additionally, locking members may be used with any type rods or dual spring member.

Preferably, a dual spring member may include provisions for increased structural stability. In some embodiments, the dual spring member may comprise a single piece of material that is coiled into an outer spring and an inner spring. In other embodiments, the dual spring member may comprise two distinct springs.

Figure 6:
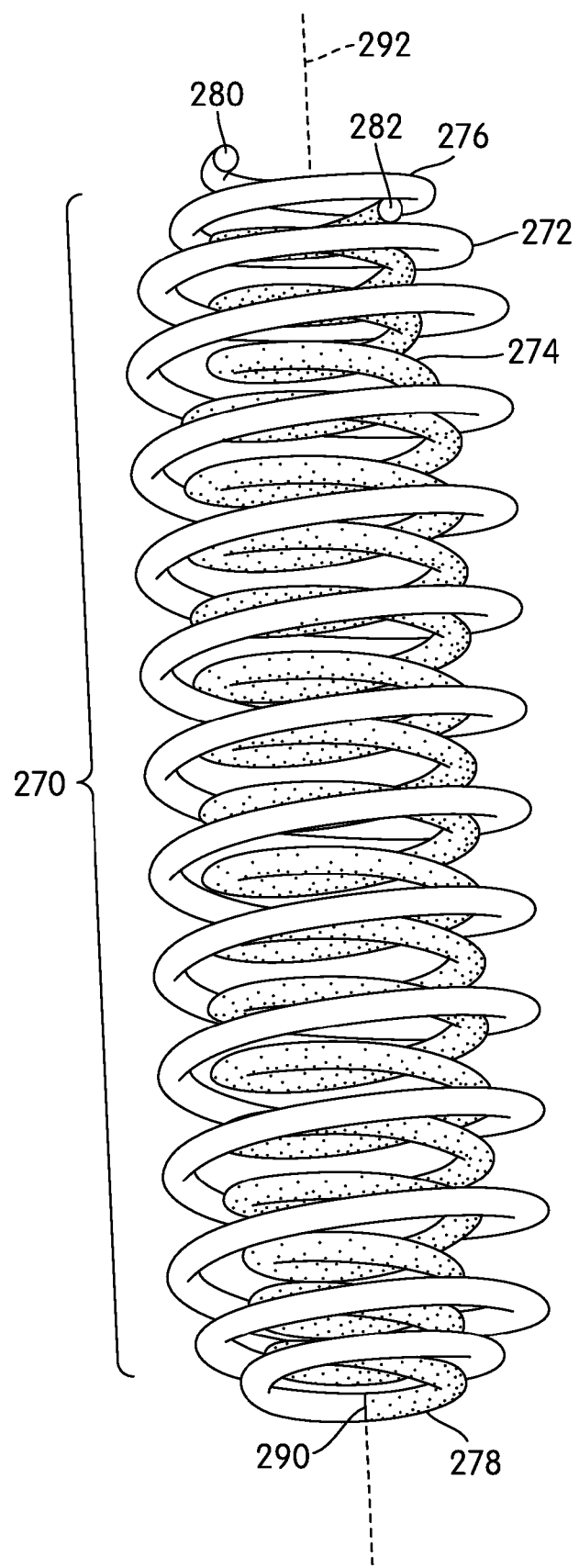
FIG. 6 is an isometric view of a preferred embodiment of a dual spring member.

FIG. 6 is an isometric view of a preferred embodiment of dual spring member 270. As previously mentioned, dual spring member 270 comprises outer spring 272 and inner spring 274. In a preferred embodiment, springs 272 and 274 comprise a single material. In other words, first end 276 of dual spring member 270 may comprise first discontinuous end 280 and second discontinuous end 282, associated with outer spring 272 and inner spring 274, respectively. Furthermore, second end 278 of dual spring member 270 does not include any discontinuous ends. Instead, outer spring 272 and inner spring 274 are joined directly at transition region 290.

It should be understood that inner spring 274 is shaded in FIG. 6 to emphasize inner spring 274 from outer spring 272. This shading is not intended to reflect any difference in material properties of springs 272 and 274, or any other physical distinctions. In a preferred embodiment, outer spring 272 and inner spring 274 comprise a single, homogenous material including substantially similar material properties. In an alternative embodiment, however, it is possible that outer spring 272 and inner spring 274 may be made of a distinct material.

Figure 7:
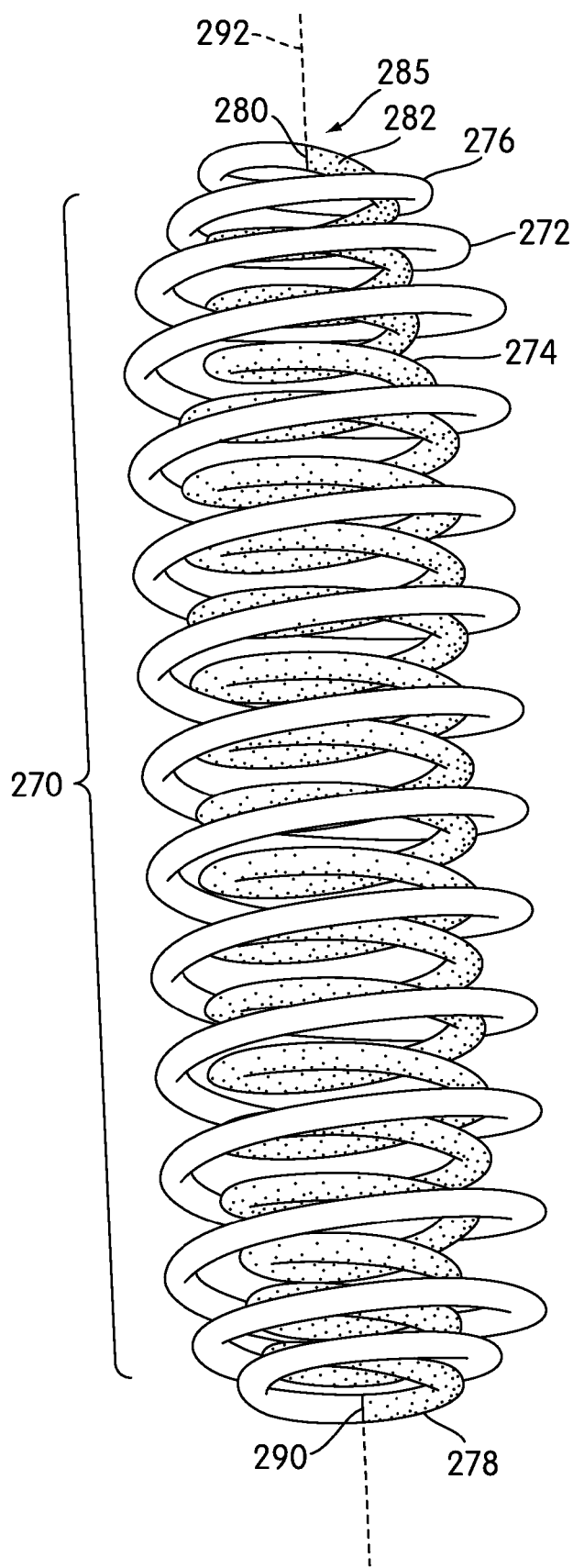
FIG. 7 is an isometric view of an alternative embodiment of a dual spring member.

It should be understood that while outer spring 272 and inner spring 274 are joined in this embodiment, in other embodiments, springs 272 and 274 may comprise separate springs that are not directly connected. Additionally, in some embodiments, springs 272 and 274 may be joined at both ends of dual spring member 270. FIG. 7 is an alternative embodiment of dual spring member 270. In this embodiment, first discontinuous end 280 and second discontinuous end 282 have been joined at first connected region 285. In some cases, ends 280 and 282 may be connected by any suitable method. In some embodiments, a low temperature bonding technique may be used. In a preferred embodiment, first connected region 285 forms a strong mechanical connection. With this alternative arrangement, stresses experienced by first end 276 and second end 278 of dual spring member 270 may be substantially equal since both ends 276 and 278 are closed with no discontinuous ends.

Figure 8:
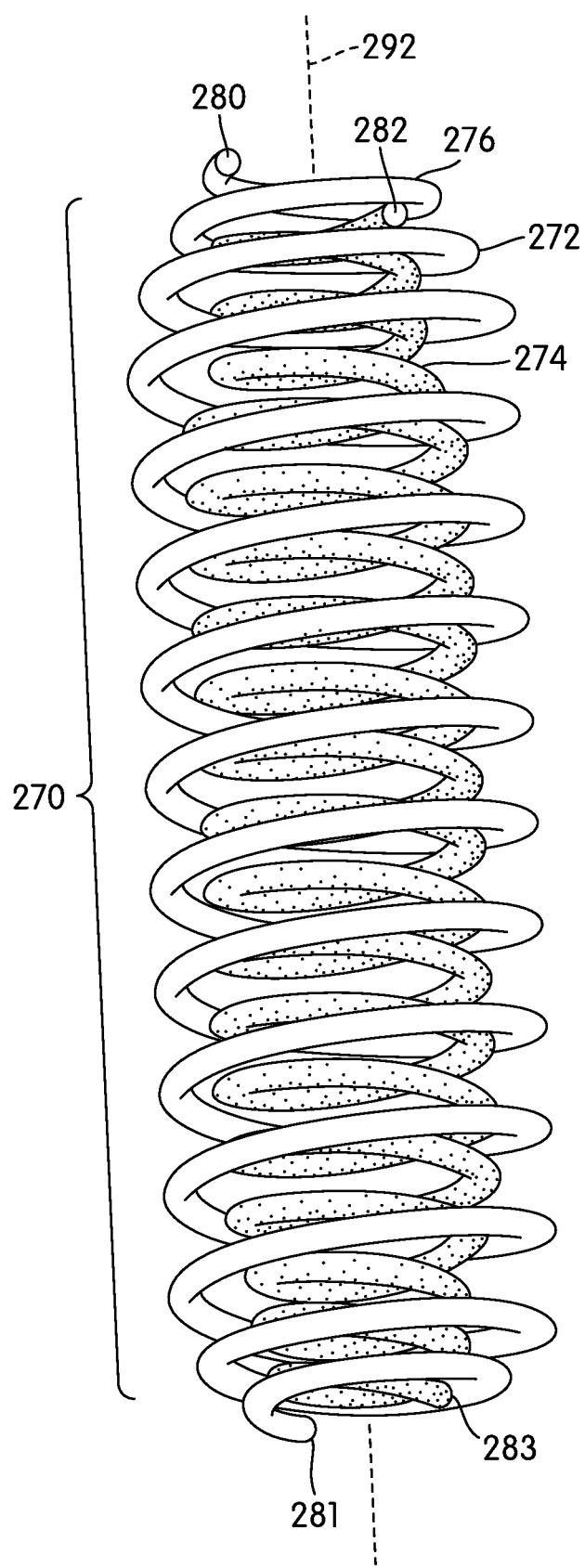
FIG. 8 is an isometric view of an alternative embodiment of a dual spring member.

FIG. 8 is another embodiment of dual spring member 270. In this embodiment, outer spring 272 and inner spring 274 are completely disconnected. In some cases, outer spring 272 includes first discontinuous end 280 and third discontinuous end 281. Also, inner spring 274 includes second discontinuous end 282 and fourth discontinuous end 283.

With this arrangement, outer spring 272 and inner spring 274 may be free to move somewhat independently of one another.

Preferably, outer spring 272 and inner spring 274 share a common central axis 292. In other words, inner spring 274 is generally concentric with outer spring 272. In other embodiments, inner spring 274 could have a central axis that is slightly misaligned with outer spring 272. Varying the position of inner spring 274 with respect to outer spring 272 may facilitate changing the flexibility properties of springs 272 and 274 in the non-axial direction. In other words, modifying the orientation of springs 272 and 274 could allow for different bending properties of dual spring member 270. In some embodiments, springs 272 and 274 could be coiled in opposing directions. This alternative arrangement could help prevent inter-digitation of springs 272 and 274.

Generally, an inner spring and an outer spring may have any cross sectional shape. In particular, the cross sectional shape of the spring wire could be circular, triangular, rectangular as well as any other polygonal or irregular shape. Additionally, the cross sectional shape of the coil, which includes the windings of the spring wire, could have any shape, including circular, triangular, rectangular as well as any polygonal or irregular shape. It is also possible to provide inner and outer springs with different sized coils or wires. In other words, the wire diameters, shapes, configurations, and sizes of the inner and outer springs may be different. By modifying the cross sectional shape and/or diameters of the spring wires and the spring coils comprising the inner and outer springs, various mechanical properties of a dual spring member can be modified.

In previous designs of spinal devices incorporating springs, the connection point of the springs could be a weak point. Often, in previous designs, springs may be attached to various rods or anchors using soldering techniques or other mechanical attachment techniques. In some cases, springs may simply be disposed against stops that prevent motion of the ends.

Preferably, a dual spring member includes provisions for securing a connection between the ends of the spring and the associated rods. In some embodiments, these connections may be made by incorporating threaded portions onto the rods that are configured to receive the ends of the dual spring member. In a preferred embodiment, these threaded portions may naturally conform to the free or natural state of the coils associated with the dual spring member.

Figure 9:
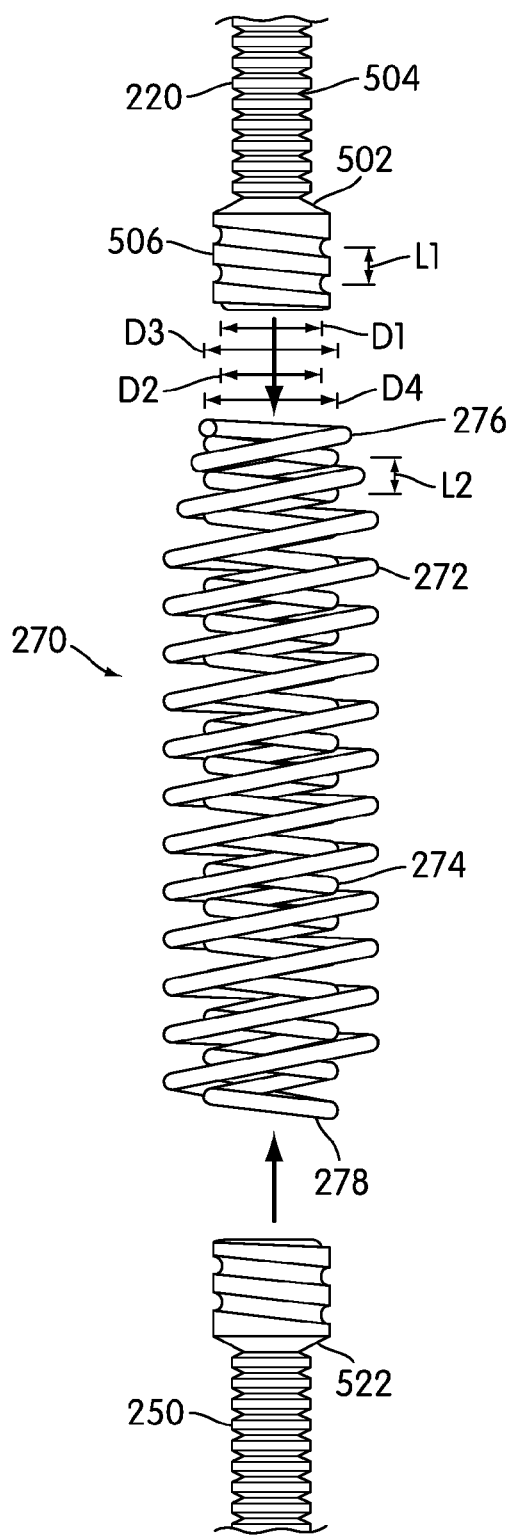
FIG. 9 is a preferred embodiment of a dual spring member attaching to two rods.
Figure 10:
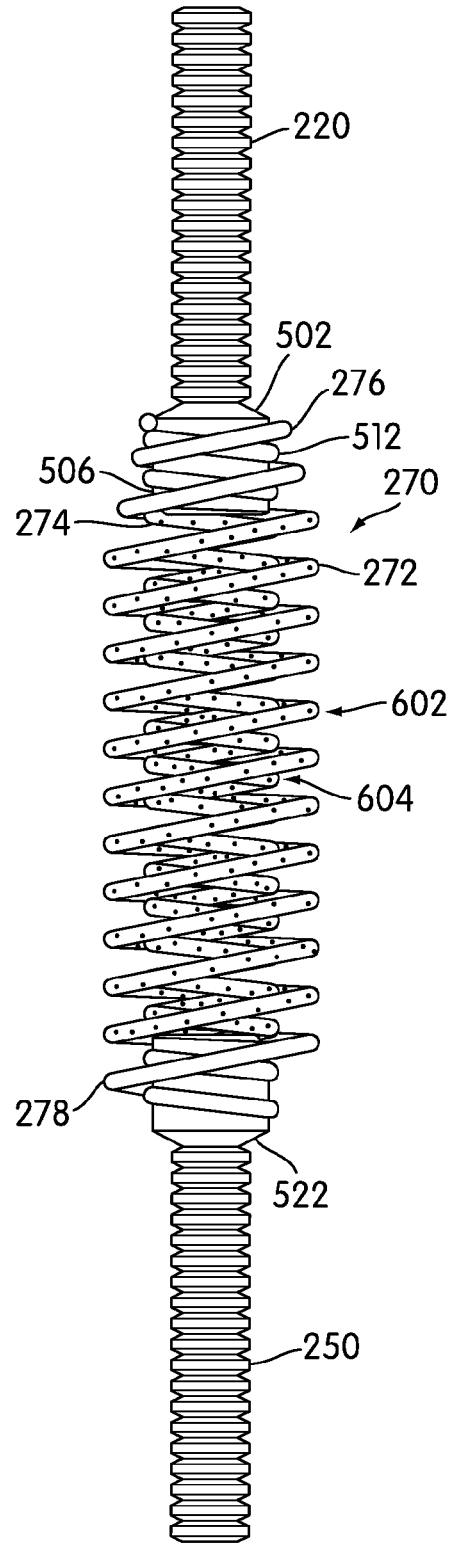
FIG. 10 is a preferred embodiment of a dual spring member attached to two rods.

FIGS. 9 and 10 illustrate a preferred method of attaching dual spring member 270 to first rod 220 and second rod 250. Preferably, first rod 220 includes first threaded portion 502. First threaded portion 502 preferably has a larger diameter than extended portion 504 of first rod 220. In a preferred embodiment, first threaded portion 502 may also include threading 506.

Preferably, first threaded portion 502 is configured to form a strong mechanical connection with first end 276 of dual spring member 270. In this embodiment, first threaded portion 502 may have a diameter D1 that is approximately equivalent to the inner diameter D2 of inner spring 274 at first end 276. Preferably, diameter D1 is associated with the base diameter of first threaded portion 502. In other words, diameter D1 is the diameter of first threaded portion 502 when threading 506 is removed. Additionally, threading 506 of first threaded portion 502 may have a diameter of D3 that is approximately equivalent to the inner diameter D4 of outer spring 272 at first end 276. In some embodiments, the spacing L1 between threading 506 may also be approximately equal to the spacing L2 between adjacent coils on inner spring 274.

Using this preferred arrangement, inner spring 274 may be configured to wrap around first threaded portion 502, between threading 506, as seen in FIG. 10. This may be achieved by screwing first threaded portion 502 together with inner spring 274. Furthermore, outer spring 272 may be wrapped around first threaded portion 502, tightly coiling around the outer surface of threading 506. In a preferred embodiment, outer spring 272 may be fixed between coils 512 of inner spring 274, thus keeping outer spring 272 fixed in place at first end 276.

Preferably, second rod 250 includes second threaded portion 522 configured to connect to second end 278 of dual spring member 270. This mechanical connection is preferably formed in a substantially similar manner to the connection between first threaded portion 502 and first end 276 of dual spring member 270.

Figure 11:
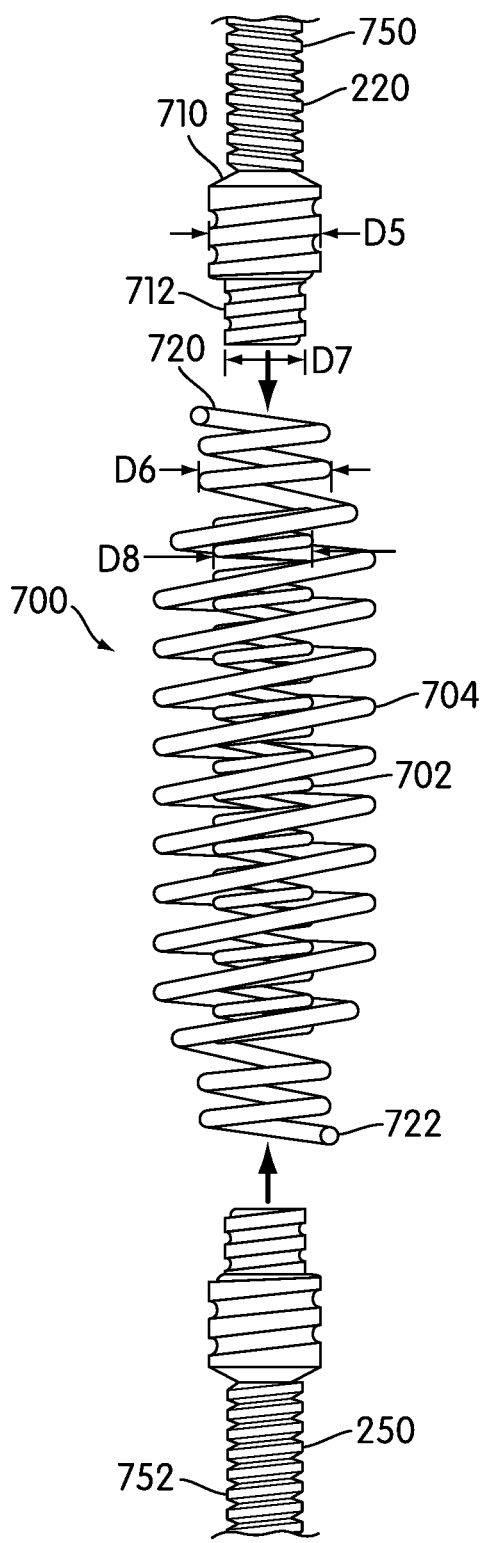
FIG. 11 is an alternative embodiment of a dual spring member attaching to two rods.
Figure 12:
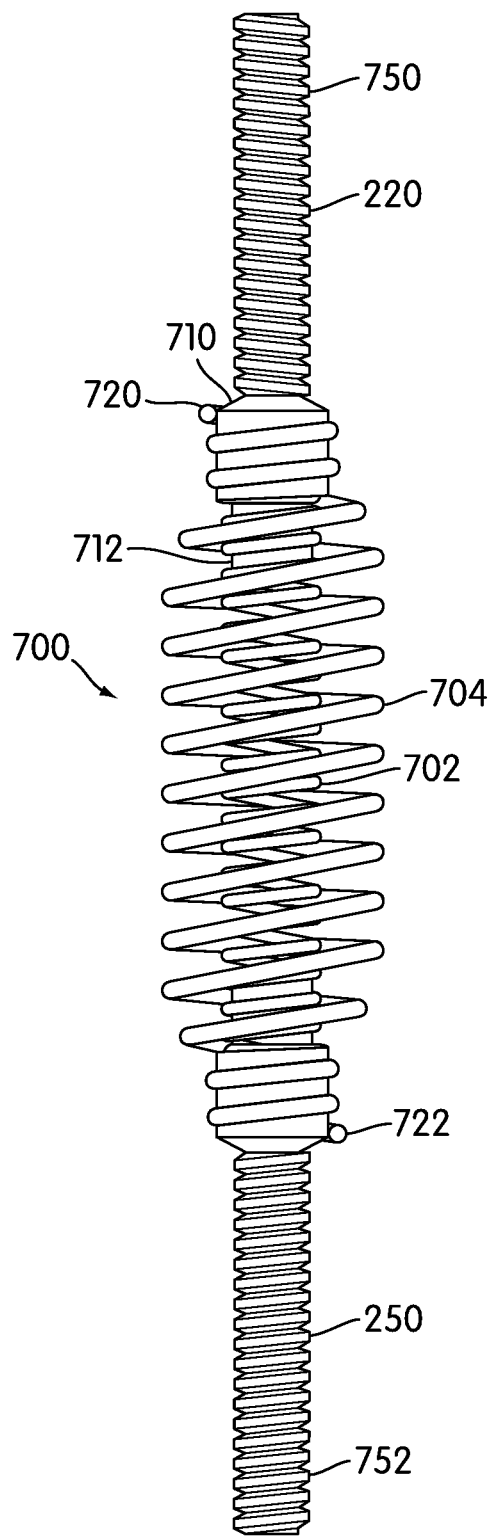
FIG. 12 is an alternative embodiment of a dual spring member attached to two rods.

In an alternative embodiment, a dual spring member could be used that incorporates two separate springs, as previously mentioned. Referring to FIGS. 11 and 12, an alternative embodiment of dual spring member 700 preferably comprises inner spring 702 and outer spring 704 that are physically separated. In order to incorporate two separate springs, a threaded portion of a rod should be modified to separately fasten to each spring 702 and 704.

The method of connecting dual spring 700 proceeds in a similar manner to the connection formed in the previous embodiment. In this case, however, first rod 220 preferably includes outer threaded portion 710 as well as inner threaded portion 712. In this embodiment, outer threaded portion 710 is configured to receive outer spring 704 at first end 720 of dual spring member 700. Likewise, inner threaded portion 712 is preferably configured to receive inner spring 702 at first end 720 of dual spring member 700.

Preferably, outer threaded portion 710 has a diameter D5 that is roughly approximate to the inner diameter D6 of outer spring 704 at first end 720. Additionally, inner threaded portion 712 has a diameter D7 that is roughly approximate to the inner diameter D8 of inner spring 702 at first end 720. In both cases, the threaded portions are sized to suitably engage and capture their respective springs. Preferably, second rod 250 includes similar provisions for fastening to second end 722 of dual spring member 700. With this arrangement, first end 720 and second end 722 of dual spring member 700 may be securely fastened to rods 220 and 250, respectively, as seen in FIG. 12.

In some embodiments, a dynamic stabilization device may include rods with threading. In the embodiment shown in FIGS. 11 and 12, first rod 220 includes first threading 750 and second rod 250 includes second threading 752. In this embodiment, first threading 750 and second threading 752 are oriented in opposing directions. Therefore, using this preferred arrangement, first rod 220 and second rod 250 may be turned with respect to dual spring member 700 to modify the tension of the dynamic stabilization device. This configuration may be similar to a turn-buckle arrangement that is found in various mechanical systems.

Figure 13:
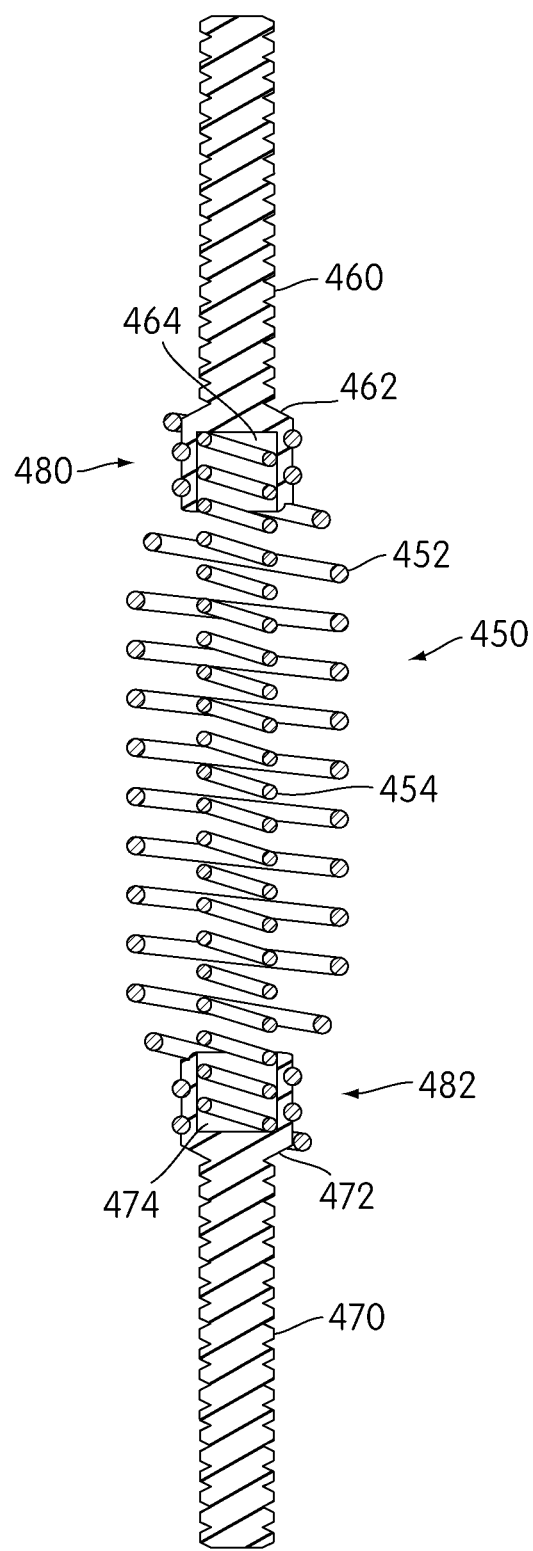
FIG. 13 is a cross sectional view of an alternative embodiment of a dual spring member attached to two rods.

FIG. 13 is a cross sectional view of another embodiment of a dual spring member connecting to rods of a dynamic stabilization device. In this embodiment, dual spring member 450 comprises outer spring 452 and inner spring 454, which are completely disconnected from one another. In some cases, first rod 460 includes first outer threaded portion 462 for receiving outer spring 452 at first side 480 of dual spring member 450. Likewise, first rod 460 includes first hollow portion 464 for receiving inner spring 454 at first side 480 of dual spring member 450. In a similar manner, second rod 470 includes second outer threaded portion 472 for receiving outer spring 452 at second side 482 of dual spring member 450. Also, second rod 470 includes second hollow portion 474 for receiving inner spring 454 at second side 482 of dual spring member 450. This arrangement provides a method of connecting dual spring member 450 to rods 460 and 470 when dual spring member 450 comprises two disconnected springs.

In a similar manner to the previous embodiments, outer threaded portions 462 and 472 may include grooves to receive outer spring 452. In some cases, hollow portions 464 and 474 may also include grooves to receive inner spring 454. Using a grooved arrangement allows springs 452 and 454 to be securely fastened with respect to rods 460 and 470. In other embodiments, hollow portions 464 and 474 may not include grooves to allow the ends of inner spring 454 to move freely. In other embodiments, outer portions 462 and 472 may not include grooves. Generally, in these embodiments, the outer spring 452 may be constrained with a cap. In these embodiments, the ends of inner spring 454 are preferably constrained within hollow portions 464 and 474.

Preferably, a dual spring member may include provisions for maintaining strength and resiliency for extended periods of time. This is necessary to ensure that stabilization to the spine is maintained over the lifetime of a patient who has a dynamic stabilization device implanted in their spine.

Preferably, the dual spring member includes provisions for preventing differential loading between the outer spring and the inner spring in order to prevent premature failure due to overloading of one spring. The term "differential loading" as used through this detailed description and in the claims refers to the tendency of one spring comprising a dual spring member to experience increased loads over a second spring. In other words, in some dual spring systems, one spring may carry a majority of the total load applied to both springs. Instead, it is preferable that a dual spring system include provisions for equally dividing the load between the two springs.

Referring back to FIGS. 9 and 10, in a preferred embodiment, outer spring 272 and inner spring 274 are configured to have equal working lengths in order to reduce or eliminate differential loading. Working length is approximately equal to the length of the portion of the spring that is able to compress. Referring to FIG. 10, the working length for outer spring 272 and inner spring 274 are associated with the portions of each spring that are free to bend and/or compress. In particular, first working portion 602 of outer spring 272 is shaded. Also, second working portion 604 of inner spring 274 is shaded.

The working length for each spring may be approximated by multiplying the diameter of each spring times the number of turns associated with free portions of the spring. Since outer spring 272 has a diameter D4 that is larger than the diameter D2 associated with inner spring 274, to achieve an approximately equal working length, inner spring 274 should include a larger number of turns along second working portion 604.

Using this preferred configuration, dual spring member 270 may be configured to reduce differential loading associated with outer spring 272 and inner spring 274. This is an important feature for a dynamic stabilization device that may be used over an extended period of time since it prevents one spring from wearing out too quickly due to overloading. Furthermore, it should be understood that these same general principles for reducing differential loads apply to alternative embodiments that incorporate separate inner and outer springs.

Preferably, dynamic stabilization device 100 is preferably configured so that dual spring member 270 never experiences a stress greater than a predetermined fatigue limit. The term 'fatigue limit' refers to a maximum amount of stress that may be applied to a material to ensure that the material does not ever experience mechanical failure.

Figure 14:
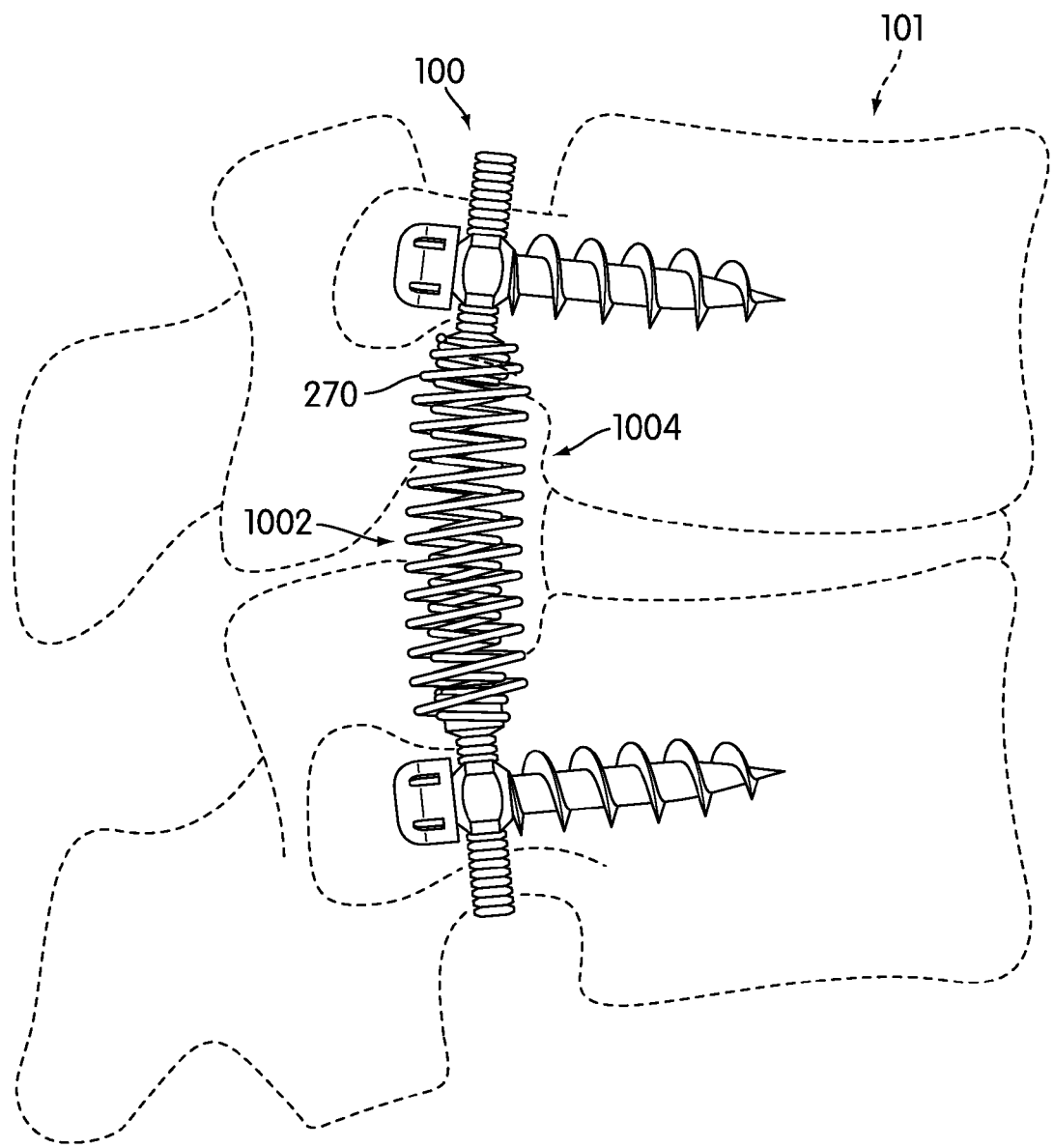
FIG. 14 is a side view of a preferred embodiment of a spine with a dynamic stabilization device including a dual spring member experiencing bending.
Figure 15:
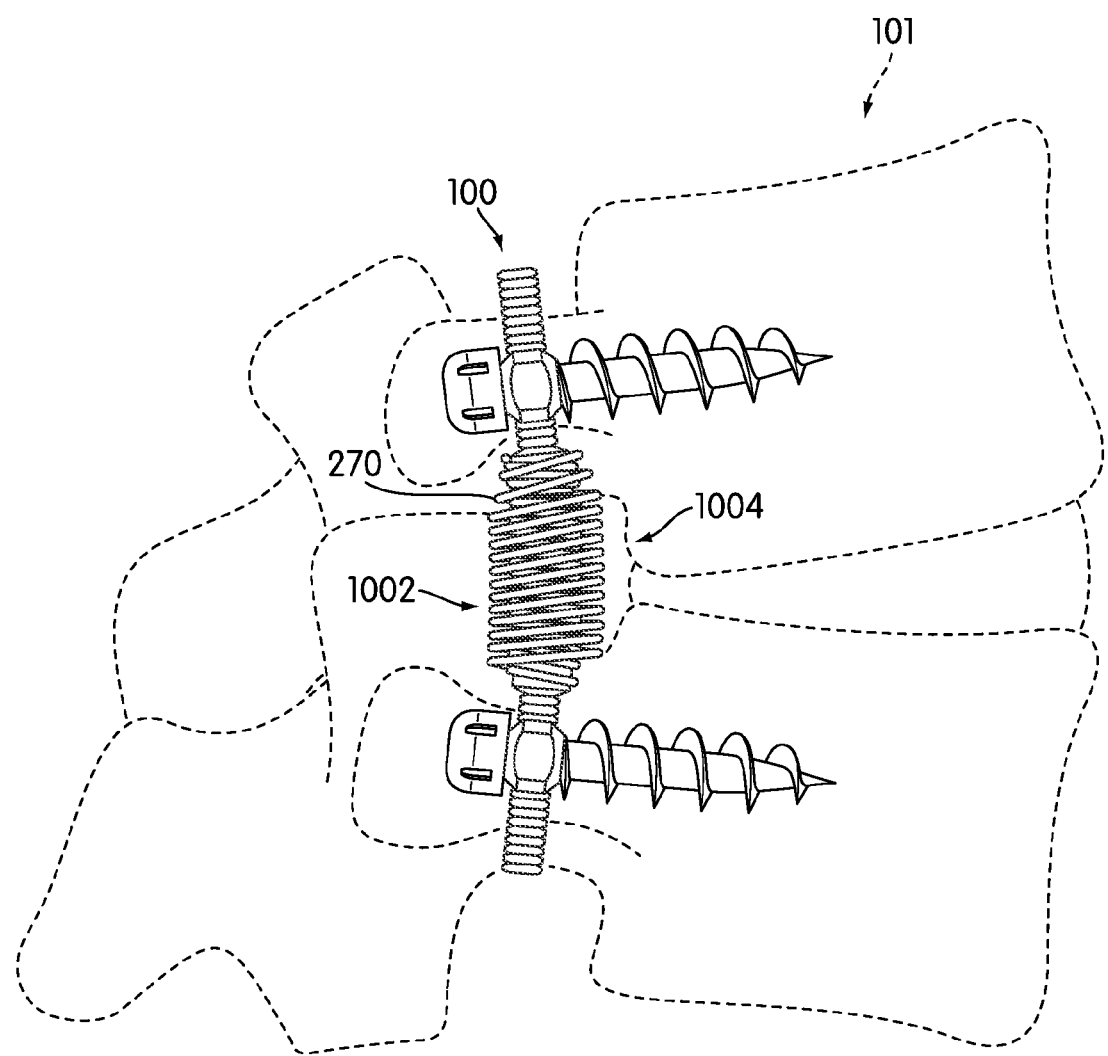
FIG. 15 is a side view of a preferred embodiment of a spine with a dynamic stabilization device including a dual spring member experiencing bending.

These various configurations of a dynamic fixation system may require a dual spring member to undergo constant bending as well as other types of stresses. FIGS. 14 and 15 depict embodiments of dual spring member 270 experiencing bending. In FIG. 14, dual spring member 270 may compress at proximal side 1004 and expand under tension at distal side 1002, as spine 101 undergoes flexion. Additionally, in FIG. 15, dual spring member 270 may expand under tension at proximal side 1004 and compress at distal side 1002, as spine 101 undergoes extension. In these positions, dual spring member 270 may experience a maximum level of load associated with bending of dual spring member 270. Because dual spring member 270 is constantly undergoing various stresses, it is preferable to construct dynamic stabilization device 100 in a manner that prevents stressing dual spring member 270 to the point of failure. Generally, dynamic stabilization device 100 may be designed so that the life expectancy of dual spring member 270 is effectively indefinite. In other words, dual spring member 270 is designed to last much longer than the life expectancy of a human patient.

Figure 16:
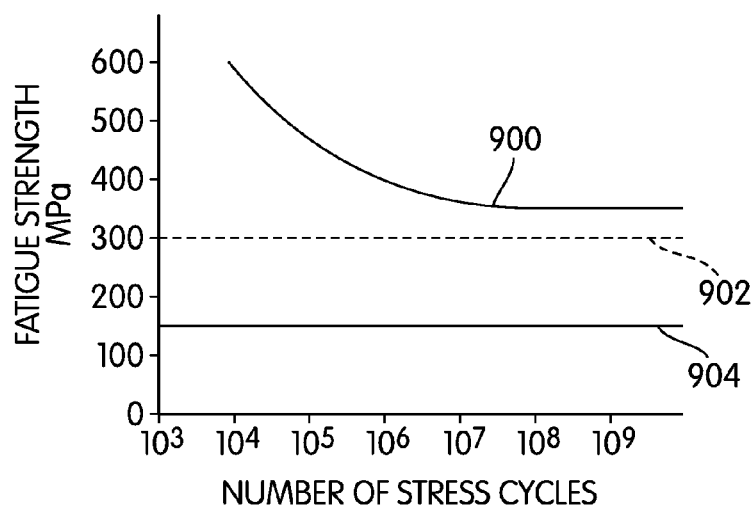
FIG. 16 is an exemplary embodiment of a relationship between fatigue strength and number of stress cycles for a dual spring member.

FIG. 16 illustrates an exemplary embodiment of a relationship between fatigue strength and number of stress cycles for dual spring member 270. Fatigue strength refers to the amount of stress applied to a material, and is characterized in the current embodiment in terms of MegaPascals (MPa). The number of stress cycles refers to the number of times a material can be stressed in a particular manner before undergoing failure. In this embodiment, the stress cycle represents a compression and re-expansion of proximal side 1004 of dual spring member 270 during flexion of spine 101, as depicted in FIG. 14. Referring to curve 900, at 600 MPa, spring 270 may undergo 10,000 cycles (compressions) before failing. Furthermore, at 400 MPa, spring 270 may undergo approximately 1,000,000 cycles (compressions) before failing.

Curve 900 follows a general pattern for a class of materials containing iron, such as steel. In particular, this relationship includes fatigue limit 902 at approximately 300 MPa. Fatigue limit 902 represents a stress level below which dual spring member 270 may be indefinitely fatigued without failing. Therefore, as long as dual spring member 270 is designed so that during operation it does not undergo compression stresses at or above 300 MPa, dual spring member 270 may continue functioning indefinitely without undergoing failure.

Preferably, to allow for some variation in experimentally determined fatigue curves as well as to provide for some change in operating conditions, a dynamic stabilization device may be defined with an effective fatigue limit. An effective fatigue limit may be used to ensure safe use of a mechanical device by designing the device to operate at stress levels far below the fatigue limit. This built in safety factor allows for some error in designing the device without risking mechanical failure. In this preferred embodiment, effective fatigue limit 904 has a value of 150 MPa, which is less than 50% of fatigue limit 902. Therefore, using this preferred arrangement, dynamic stabilization device 100 may be designed so that dual spring member 270 never experiences stresses above effective fatigue limit 904 to ensure indefinite durability of dual spring member 270.

It should be understood that curve 900 is only intended to be exemplary. The values discussed here, especially the value 150 MPa for an effective fatigue limit associated with compressive and tension forces, are only intended to illustrate the concept of choosing an effective fatigue limit that is far less (around 50%) than the fatigue limit. Furthermore, although this embodiment illustrates an effective fatigue limit for the compression and tension of dual spring member 270, effective fatigue limits for tensile stresses and shear stresses are also preferably considered in constructing dynamic stabilization device 100. In other words, the stresses applied to dual spring member 270 as it is stretched and bent should also be below associated effective fatigue limits at all times to ensure that dual spring member 270 never undergoes failure.

Using this preferred arrangement, dynamic stabilization device 100 may be configured to function for an indefinite period of time by ensuring that dual spring member 270 never experiences stresses greater than effective fatigue limit 904. In other words, dynamic stabilization device 100 may be designed so that under normally expected physiological loads, dual spring member 270 will not be stressed beyond effective fatigue limit 904. This feature of durability when coupled with the provision to reduce differential loading preferably helps to maintain the structural integrity of dynamic stabilization device 100 indefinitely. This preferably allows dynamic stabilization device 100 to function for the lifetime of a patient, ensuring the stability of the spine over this period.

Figure 17:
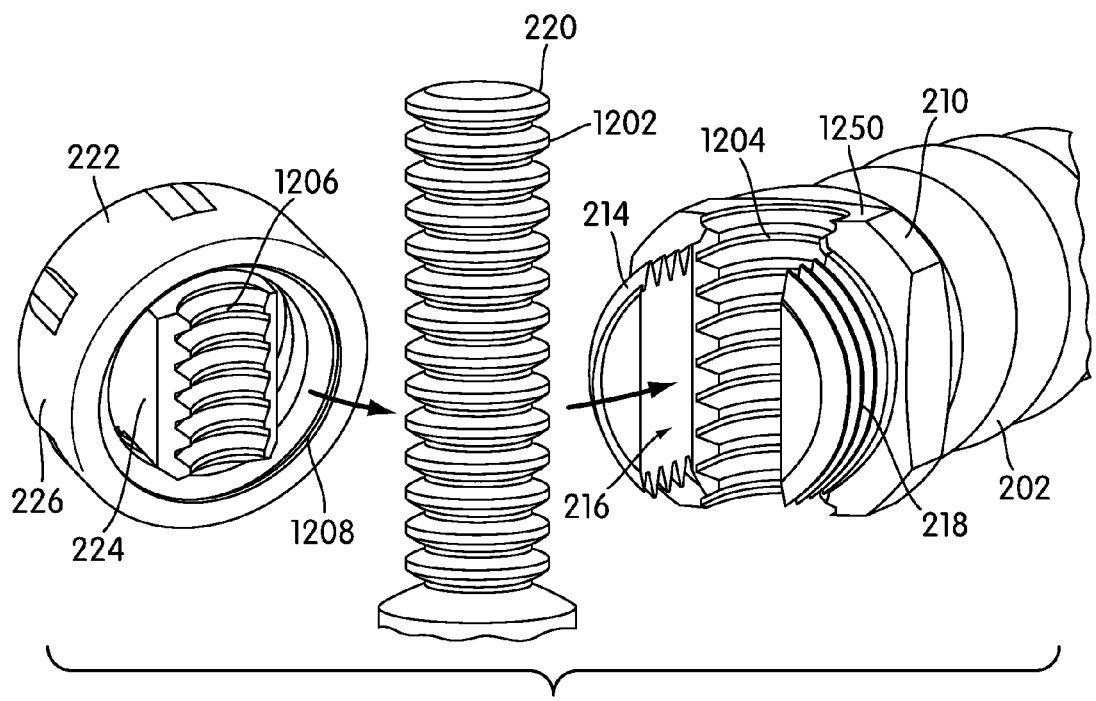
FIG. 17 is a preferred embodiment of a connection between a rod and an anchor.

Preferably, a dynamic stabilization device includes provisions for securely fastening rods in place with respect to bone anchors as well as provisions for facilitating fine tuned adjustments to a spanning length between two anchors. FIG. 17 illustrates a preferred embodiment of the connection between first rod 220 and first anchor 202. First rod 220 is configured to insert into first slotted portion 216 of first anchor head 214. In a preferred embodiment, first rod 220 includes ridges 1202 that are configured to rest within first recesses 1204 disposed within first slotted portion 216.

In this preferred embodiment, first recesses 1204 of first slotted portion 216 may be disposed within first drive receiving surface 210. In particular, first slotted portion 216 cuts through second flat side 1250 of first drive receiving surface 210. Similarly, first slotted portion 216 cuts through a flat side disposed opposite of second flat side 1250. This preferred arrangement allows for increased strength and durability of dynamic stabilization device 100, as first rod 220 may be fixed in place just above where first anchor 202 is driven into bone, thus reducing the moment arm and the forces experienced by dynamic stabilization device 100. In still other embodiments, first recessed 1204 and first slotted portion 216 may be disposed above first drive receiving surface 210. This arrangement may provide an increased moment arm, which can be used to correct deformities.

Once first rod 220 is inserted into first slotted portion 216, first cap 222 may be attached to first anchor head 214. In this embodiment, first inner cap 224 is disposed within first outer cap 226. First inner cap 224 includes second recesses 1206 configured to engage ridges 1202. Additionally, first outer cap 226 includes cap threading 1208 configured to screw onto first anchor threading 218. Therefore, as first cap 222 is screwed into place, first rod 220 is locked into place with respect to first anchor 202.

Although this embodiment includes the attachment of first rod 220 to first anchor 202, it should be understood that a similar procedure is used to attach second rod 250 to second anchor 204. Using the preferred configuration, first anchor 202 and second anchor 204 can be secured via rods 220 and 250, respectively, to dual spring member 270.

Preferably, this method of attachment allows a surgeon to fine tune the distance between first anchor 202 and second anchor 204, as the anchors 202 and 204 may be moved with respect to rods 220 and 250 in increments associated with the distance between ridges 1202. In some embodiments, the spacing between ridges 1202 may be made small so that very fine adjustments may be made. Furthermore, because of the nature of the connection, rods 220 and 250 will not slip with respect to anchors 202 and 204, thus preserving the initially selected length indefinitely.

In some embodiments, the shape of ridges associated with a rod may be modified. In some cases, the cross-sectional shape of the ridges could be sinusoidal, box-like, triangular, rounded or any pattern. In other cases, a rod may not include any ridges, but instead may be smooth. In still other embodiments, a rod may include various textures such as a knurling pattern. In these embodiments, components of the dynamic stabilization device that are configured to engage the rod may also include textured patterns to provide frictional connections between the confronting surfaces of the rod and the adjacent components. Additionally, a rod could include threading so that the distance between the rods can be moved by turning them, as was discussed in a previous embodiment.

Figure 18:
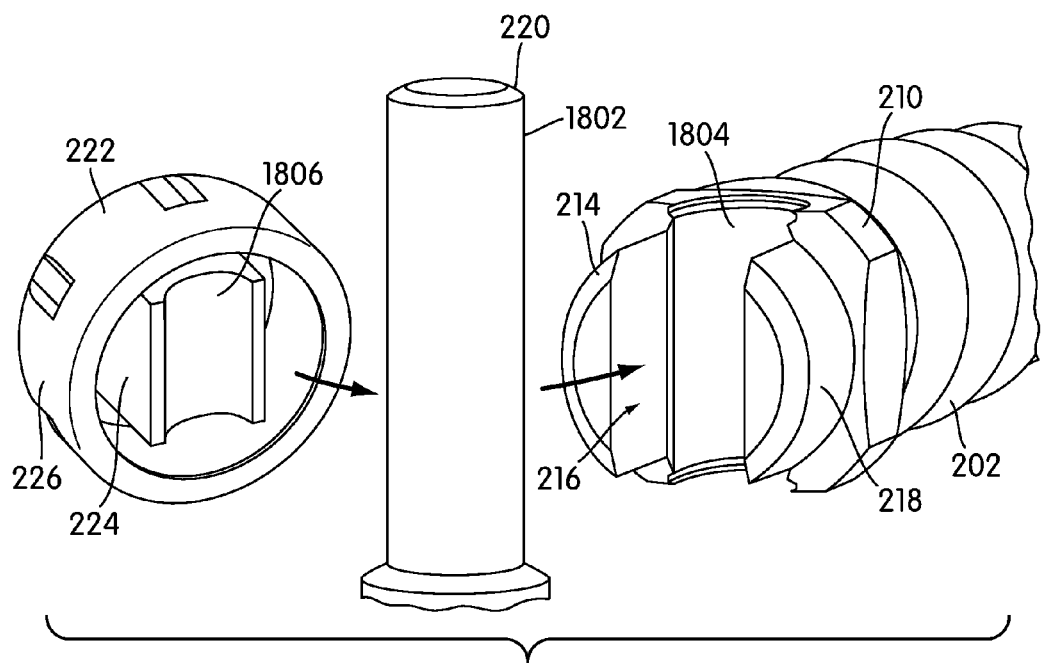
FIG. 18 is an alternative embodiment of a connection between a rod and an anchor.
Figure 19:
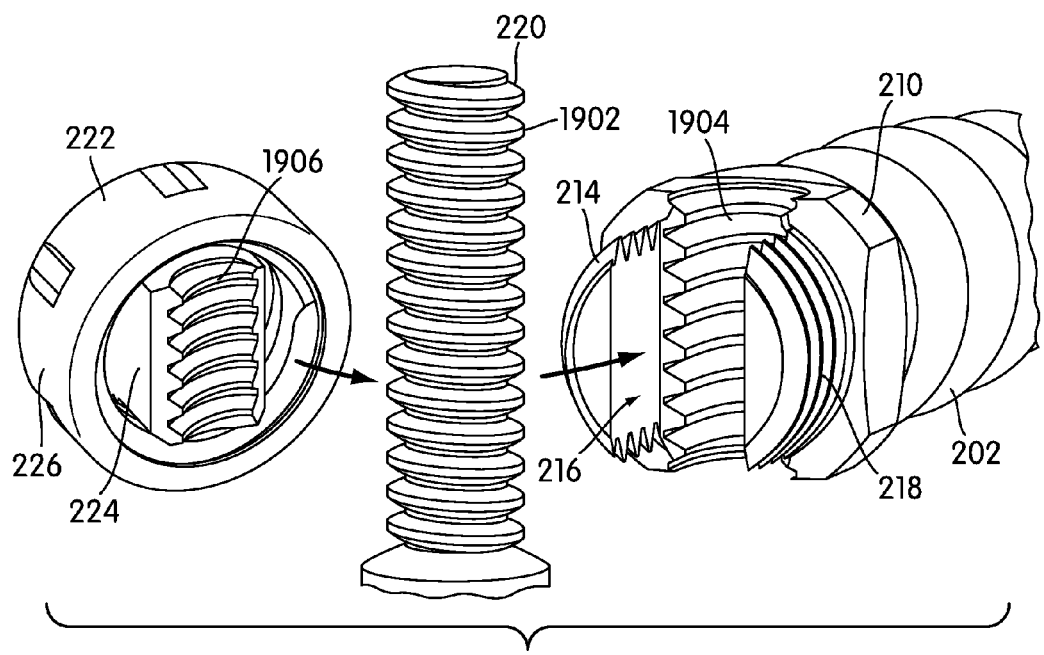
FIG. 19 is an alternative embodiment of a connection between a rod and an anchor.

FIGS. 18 and 19 illustrate alternative embodiments of a rod used with a dynamic stabilization device. In FIG. 18, first rod 220 preferably includes smooth surface 1802. In this embodiment, first cap 222 may be configured with smooth recess 1806 to receive smooth surface 1802. Likewise, first slotted portion 216 may include smooth recessed portion 1804. In FIG. 19, first rod 220 preferably includes threading 1902. Preferably, first cap 222 is configured with first threaded recesses 1906 to receive threading 1902. Likewise, first slotted portion 216 may include second threaded recesses 1904 to receive threading 1902. With this arrangement, first rod 220 may be configured to turn with respect to first cap 222 and first anchor 202. This threaded arrangement allows for additional adjustments of first rod 220 after the dynamic stabilization device has been assembled. Although only first rod 220 is shown in FIGS. 18 and 19, these alternative surfaces could also be applied to second rod 250.

Generally, dual spring member 270 will undergo various stresses following implantation into a spine. Initially, referring to FIG. 1, dynamic stabilization device 100 is in a rest position associated with a generally straightened position of spine 101. In this rest position, dual spring member 270 may experience some minimum level of load due to the stresses applied to dual spring member 270 in this position. However, in other embodiments, it is possible to install stabilization device 100 with either an initial compression or tension. In other words, stabilization device 100 includes some kind of pre-stress, either residual compression or residual tension. It is also possible to load different portions of the vertebral bodies with unequal or opposite forces. This arrangement may be used to correct or treat deformities, such as scoliosis or spondylolisthesis.

For example, to correct scoliosis, a stabilization system including two stabilization devices may be attached to two adjacent vertebrae. These two dynamic stabilization devices may include different residual stresses, one stabilization device including residual tension and the second stabilization device including residual compression. This arrangement can apply a rotational force to the adjacent vertebrae whereby scoliosis may be corrected or stabilized.

In another example, to correct spondylolisthesis, a stabilization system including two stabilization devices may be attached to two adjacent vertebrae. These two dynamic stabilization devices may include substantially similar residual stresses, both stabilization devices including residual tension. This arrangement can apply a translational force to the adjacent vertebrae whereby spondylolisthesis may be corrected or stabilized. This motion can be demonstrated by comparing FIG. 14 to FIG. 1, where FIG. 14 is the initial position, and FIG. 1 is the resulting, treated position.

In another example, to correct spinal stenosis, a stabilization system including two stabilization devices may be attached to two adjacent vertebrae. These two dynamic stabilization devices may include substantially similar residual stresses, both stabilization devices including residual compression. This arrangement can apply a flexion force to the adjacent vertebrae whereby stenosis may be corrected or stabilized. This motion can be demonstrated by comparing FIG. 15 to FIG. 1, where FIG. 15 is the initial position, and FIG. 1 is the resulting, treated position. In another case, this motion can be demonstrated by comparing FIG. 1 to FIG. 14, where FIG. 1 is the initial position, and FIG. 14 is the resulting, treated position.

In a final example, to correct scoliosis, a stabilization system including two stabilization devices may be attached to two adjacent vertebrae. These two dynamic stabilization devices may include two different residual stresses, with a first stabilization device including a residual compression and a second stabilization device including a residual tension. This arrangement can apply both compression and tension forces to the adjacent vertebrae whereby scoliosis may be corrected or stabilized.

Figure 20:
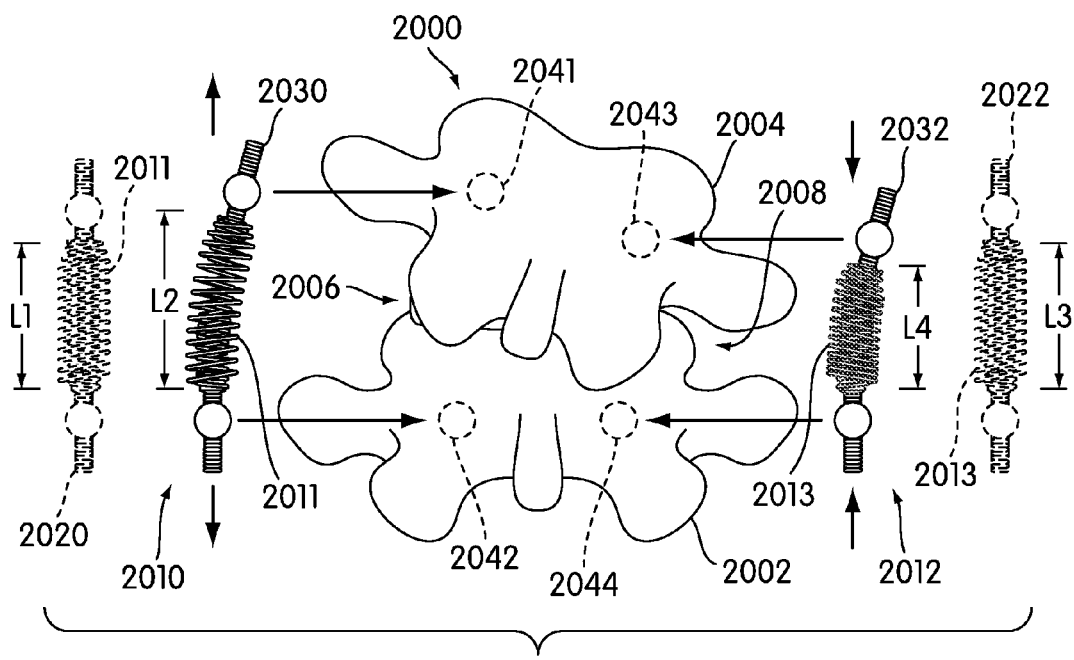
FIG. 20 is a preferred embodiment of two dynamic stabilization devices undergoing pre-tensioning and pre-compression.

Referring to FIG. 20, second vertebrae 2004 may be bent or curved with respect to first vertebrae 2002 along a portion of spine 2000 that is deformed due to scoliosis. Although this exemplary embodiment includes a rightwards leaning of second vertebrae 2004, it should be understood that in other cases, a vertebrae could be leftwards leaning. Additionally, in some cases, the vertebrae may also lean forwards or twist with respect to an adjacent vertebrae. Each of these different configurations associated with scoliosis may be generally treated using similar principles as those discussed for the current embodiment.

In some embodiments, first stabilization device 2010 may be associated with first side 2006 of spine 2000. In this embodiment, first stabilization device 2010 has a first initial position 2020 that is associated with a free or unstressed state of first dual spring member 2011. Additionally, second stabilization device 2012 may be associated with second side 2008 of spine 2000. In this embodiment, second stabilization device 2012 has a second initial position 2022 that is associated with a free or unstressed state of second dual spring member 2013.

In some embodiments, stabilization devices 2010 and 2012 may be pre-stressed before being attached to vertebrae 2002 and 2004. In the current embodiment, first stabilization device 2010 may undergo a pre-tension that causes first stabilization device 2010 to stretch from first initial position 2020 to first stressed position 2030. At this point, first dual spring member 2011 has preferably expanded from first original length L1 to first modified length L2. Following this, first stabilization device 2010 may be attached to first vertebrae 2002 at first attachment point 2042 and to second vertebrae 2004 at second attachment point 2041.

In this embodiment, second stabilization device 2012 may undergo a pre-compression that squeezes second stabilization device 2012 from a second initial position 2022 to a second stressed position 2032. At this point, second dual spring member 2013 has preferably contracted from second original length L3 to second modified length L4. Following this, second stabilization device 2012 may be attached to first vertebrae 2002 at third attachment point 2044 and to second vertebrae 2004 at fourth attachment point 2043.

Figure 21:
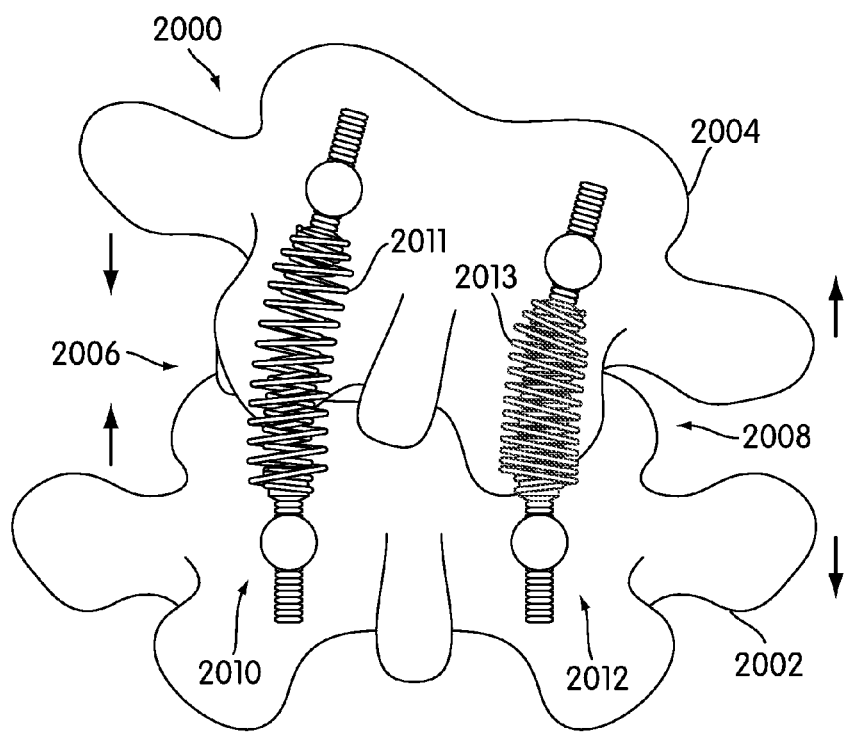
FIG. 21 is a preferred embodiment of two dynamic stabilization devices configured to correct scoliosis.

Referring to FIG. 21, as stabilization devices 2010 and 2012 are attached to vertebrae 2002 and 2004 in pre-stressed conditions, dual spring members 2011 and 2013 may be configured to apply compressive forces and tension forces, respectively, to vertebrae 2002 and 2004. In particular, first dual spring member 2011 may act to pull first vertebrae 2002 and 2004 together at first side 2006. Additionally, second dual spring member 2013 may act to separate vertebrae 2002 and 2004 at second side 2008. This general arrangement may help to realign spine 2000 over time, as vertebrae 2002 and 2004 are generally straightened with respect to one another.

Figure 22:
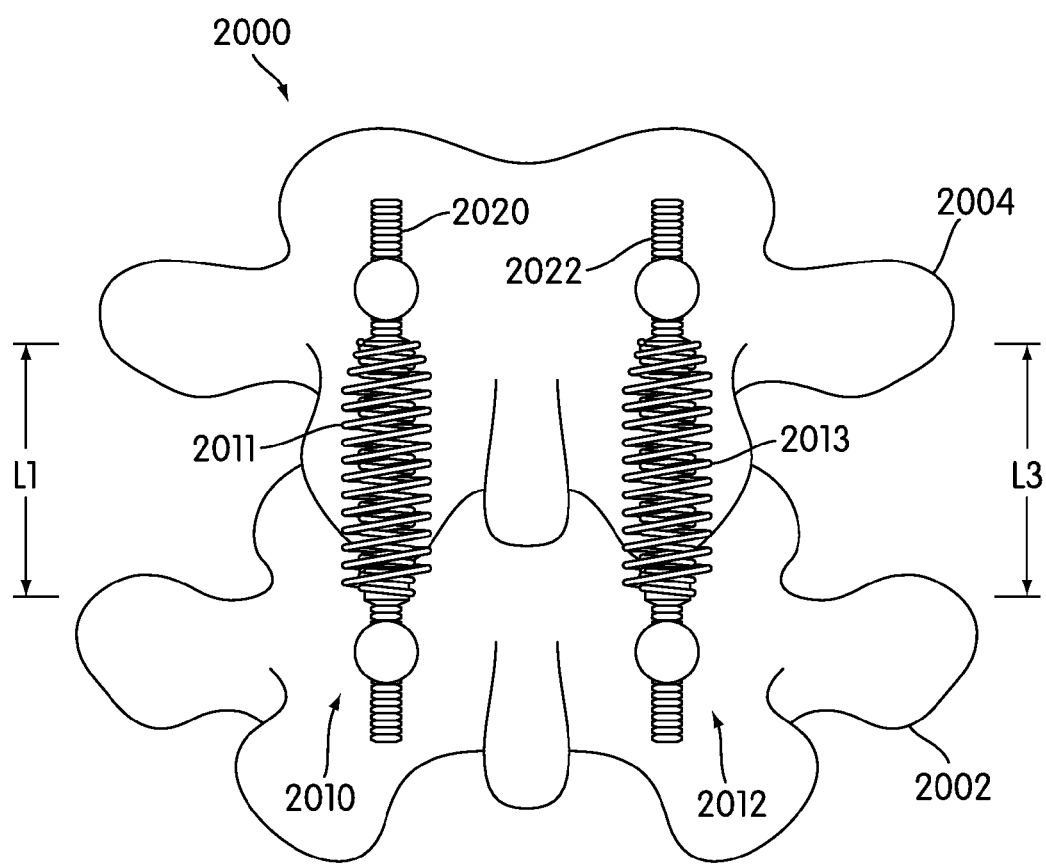
FIG. 22 is a preferred embodiment of two dynamic stabilization devices with dual spring members in unstressed positions.

FIG. 22 is a preferred embodiment of vertebrae 2002 and 2004 in proper alignment. In some cases, when vertebrae 2002 and 2004 have been properly aligned, stabilization devices 2010 and 2012 return to initial positions 2020 and 2022, respectively. In these initial positions 2020 and 2022, dual spring members 2011 and 2013 may have first initial length L1 and second initial length L3, respectively. This arrangement may prevent overcorrection since dual spring members 2011 and 2013 are no longer stressed and therefore will no longer apply forces to vertebrae 2002 and 2004 once vertebrae 2002 and 2004 have been properly aligned. However, in some cases, for example, in a fixed deformity, even after dual spring members 2011 and 2013 return to their initial lengths, the dual spring members may continue to apply a corrective force to vertebrae 2002 and 2004.

Using these various provisions discussed throughout this detailed description preferably improves the performance of a dynamic stabilization device. In particular, the resistance to differential loading and the design to maintain stresses below a predefined effective fatigue limit may increase the lifetime of dynamic stabilization device 100.

The materials used to make a dynamic stabilization device may vary from one embodiment to another embodiment. Preferably, materials used to construct the various components are rigid and may be designed to endure the harsh environment of the human body. Materials used for anchors (including screws and hooks), rods and various other components are well known in the art. Preferably, the materials used to construct a dual spring member are also relatively flexible to provide for some deflection of the inner and outer springs.

While various embodiments of the invention have been described, the description is intended to be exemplary, rather than limiting and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims.

What is claimed is:

1. A dynamic stabilization device configured for implantation into a spine, comprising:
   an outer coil spring;
   an inner coil spring inside the outer coil spring;
   a first rod; and a second rod, wherein the outer coil spring has a first working length;

wherein the first working length is a length through which the outer coil spring extends through turns along a free portion of the outer coil spring over which the outer coil spring is free to bend or compress;

wherein the outer coil spring has a first end portion and a second end portion opposite to the first end portion of the outer coil spring, the free portion of the outer coil spring disposed between the first and second end portions of the outer coil spring;

wherein the first and second end portions of the outer coil spring are attached to the first and second rods, respectively, such that the outer coil spring undergoes compression under compressive loading between the first and second rods and tension under tensile loading between the first and second rods;

wherein the inner coil spring has a second working length;

wherein the second working length is a length through which the inner coil spring extends through turns along a free portion of the inner coil spring over which the inner coil spring is free to bend or compress;

wherein the inner coil spring has a first end portion and a second end portion opposite to the first end portion of the inner coil spring, the free portion of the inner coil spring disposed between the first and second end portions of the inner coil spring;

wherein the first and second end portions of the inner coil spring are attached to the first and second rods, respectively, such that the inner coil spring undergoes compression under compressive loading between the first and second rods and tension under tensile loading between the first and second rods; and wherein the first working length is substantially equal to the second working length.

2. The dynamic stabilization device according to claim 1, wherein the number of turns along the free portion of the inner coil spring is greater than the number of turns along the free portion of the outer coil spring.

3. The dynamic stabilization device according to claim 1, wherein the outer coil spring has a first wire diameter along the first working length and the inner coil spring has a second wire diameter along the second working length, and wherein the first wire diameter is different from the second wire diameter.

4. The dynamic stabilization device according to claim 1, wherein coils of a first end of the outer coil spring and coils of a first end of the inner coil spring are threaded onto the first grooves of the first rod; and wherein coils of a second end of the outer coil spring and coils of a second end of the inner coil spring are threaded onto second grooves of the second rod.

5. The dynamic stabilization device according to claim 4, further comprising:

a first anchor attached to the first rod and configured to attach to a first lateral portion of a first vertebra of the spine;

a second anchor attached to the second rod and configured to attach to a second lateral portion of a second vertebra; and wherein the first and second lateral portions are on the same side of a central spinous process of the respective first and second vertebrae.

6. The dynamic stabilization device according to claim 4, wherein the first grooves of the first rod comprise inner grooves and outer grooves;

wherein the coils of the first end of the inner spring are threaded onto the inner grooves; and wherein the coils of the first end of the outer spring are threaded onto the outer grooves.

7. The dynamic stabilization device according to claim 1, further comprising:

a first anchor configured to attach to a first vertebra of the spine;

a second anchor configured to attach to a second vertebra of the spine;

wherein the outer coil spring and the inner coil spring extend between the first anchor and the second anchor;

wherein the first rod is adjustably attached to the first anchor;

wherein the second rod is adjustably attached to the second anchor;

wherein the first rod and the second rod each have a plurality of first incremental adjustment structures;

wherein the first anchor and the second anchor each have a plurality of second incremental adjustment structures complementary to the first incremental adjustment structures; and wherein the outer coil spring and the inner coil spring are stressed by moving the first anchor and the second anchor relative to the respective first and second rods in increments associated with the plurality of first incremental adjustment structures and the plurality of second incremental adjustment structures.

8. The dynamic stabilization device according to claim 7, wherein the first incremental adjustment structures comprise separate annular ridges around the first rod and the second rod; and wherein the second incremental adjustment structures comprise internal annular recesses on the first anchor and the second anchor.

9. The dynamic stabilization device according to claim 1, wherein the first end portion of the inner coil spring is configured to attach to a first threaded portion of the first rod of the dynamic stabilization device and the first end portion of the outer coil spring is configured to attach to a second threaded portion of the first rod of the dynamic stabilization device, the first threaded portion of the first rod differing from the second threaded portion of the first rod; and wherein the second end portion of the inner coil spring is configured to attach to a first threaded portion of the second rod of the dynamic stabilization device and the second end portion of the outer coil spring is configured to attach to a second threaded portion of the second rod of the dynamic stabilization device, the first threaded portion of the second rod differing from the second threaded portion of the second rod.

10. The dynamic stabilization device according to claim 1, wherein the first rod is attached to a first anchor configured for implantation into a first vertebra, and wherein the second rod is attached to a second anchor configured for implantation into a second vertebra.

11. A dynamic stabilization device configured for implantation into a spine, comprising:

an outer coil spring;

an inner coil spring inside the outer coil spring;

wherein the outer coil spring has a first working length;

wherein the first working length is a length through which the outer coil spring extends through turns along a free portion of the outer coil spring over which the outer coil spring is free to bend or compress;

wherein the inner coil spring has a second working length;

wherein the second working length is a length through which the inner coil spring extends through turns along a free portion of the inner coil spring over which the inner coil spring is free to bend or compress;
wherein the first working length is substantially equal to the second working length;
a first rod having first grooves;
a second rod having second grooves;
wherein coils of a first end of the outer coil spring and coils of a first end of the inner coil spring are threaded onto the first grooves of the first rod;
wherein coils of a second end of the outer coil spring and coils of a second end of the inner coil spring are threaded onto the second grooves of the second rod;
a first locking member attached to the first rod adjacent to the first grooves of the first rod;
wherein the first locking member contacts at least one of the coils of the first end of the outer coil spring and the coils of the first end of the inner coil spring to limit further motion of the first ends of the outer and inner coil springs onto the first rod;
a second locking member attached to the second rod adjacent to the second grooves of the second rod; and
wherein the second locking member contacts at least one of the coils of the second end of the outer coil spring and the coils of the second end of the inner coil spring to limit further motion of the second ends of the outer and inner coil springs onto the second rod.

12. A dynamic stabilization device configured for implantation into a spine, comprising:
a dual spring member including a first end, a second end, an outer coil spring, and an inner coil spring inside the outer coil spring;
a first rod;
wherein the outer coil spring at the first end of the dual spring member is attached to the first rod at a first connection;
wherein the inner coil spring at the first end of the dual spring member is attached to the first rod at a second connection;
a second rod;
wherein the outer coil spring at the second end of the dual spring member is attached to the second rod at a third connection;
wherein the inner coil spring at the second end of the dual spring member is attached to the second rod at a fourth connection;
wherein the outer coil spring has a first working length from the first connection to the third connection;
wherein the first working length is a length through which the outer coil spring extends through turns along a free portion of the outer coil spring between the first connection and the third connection over which the outer coil spring is free to bend or compress;
wherein under compression loading the first rod and the second rod push the outer coil spring at the first connection and the third connection respectively;
wherein under tensile loading the first rod and the second rod pull the outer coil spring at the first connection and the third connection respectively;
wherein the inner coil spring has a second working length from the second connection to the fourth connection;
wherein the second working length is a length through which the inner coil spring extends through turns along a free portion of the inner coil spring between the second connection and the fourth connection over which the inner coil spring is free to bend or compress;
wherein under compression loading the first rod and the second rod push the inner coil spring at the second connection and the fourth connection respectively;
wherein under tensile loading the first rod and the second rod pull the inner coil spring at the second connection and the fourth connection respectively; and
wherein the first working length is substantially equal to the second working length.

13. The dynamic stabilization device according to claim 12, wherein the number of turns along the free portion of the inner coil spring is greater than the number of turns along the free portion of the outer coil spring.

14. The dynamic stabilization device according to claim 12, wherein the outer coil spring has a first wire diameter along the first working length and the first inner coil spring has a second wire diameter along the second working length, and wherein the first wire diameter is different from the second diameter.

15. The dynamic stabilization device according to claim 12, further comprising:
a first anchor configured to attach to a first vertebra of the spine;
a second anchor configured to attach to a second vertebra of the spine;
wherein the outer coil spring and the inner coil spring extend between the first anchor and the second anchor;
wherein the first rod is adjustably attached to the first anchor;
wherein the second rod is adjustably attached to the second anchor;
wherein the first rod and the second rod each have a plurality of first incremental adjustment structures;
wherein the first anchor and the second anchor each have a plurality of second incremental adjustment structures complementary to the first incremental adjustment structures; and
wherein the outer coil spring and the inner coil spring are stressed by moving the first anchor and the second anchor relative to the respective first and second rods in increments associated with the plurality of first incremental adjustment structures and the plurality of second incremental adjustment structures.

16. The dynamic stabilization device according to claim 15, wherein the first incremental adjustment structures comprise separate annular ridges around the first rod and the second rod; and
wherein the second incremental adjustment structures comprise internal annular recesses on the first anchor and the second anchor.

17. The dynamic stabilization device according to claim 12, wherein the outer coil spring extends in a direction from the first end to the second end a distance that is longer than a distance that the inner coil spring extends in the direction from the first end to the second end;
wherein the first rod includes a first threaded portion and a second threaded portion different from the first threaded portion;
wherein the second threaded portion is disposed at a distal end of the first rod and the first threaded portion is disposed at an intermediate portion of the first rod;
wherein the first threaded portion and the second threaded portion are disposed in series longitudinally along the first rod;
wherein the first threaded portion has a first diameter and the second threaded portion has a second diameter;
wherein the first diameter is greater than the second diameter;

wherein the first connection comprises a first threaded connection at the first end of the dual spring member between the first threaded portion of the first rod and the outer coil spring; and wherein the second connection comprises a second threaded connection at the first end of the dual spring member between the second threaded portion of the first rod and the inner coil spring.

18. A dynamic stabilization system configured for implantation into a spine, comprising:

a first dynamic stabilization device comprising:
a first dual spring member including a first outer coil spring and a first inner coil spring inside the first outer coil spring;
wherein the first outer coil spring has a first working length;
wherein the first working length is a length through which the first outer coil spring extends through turns along a free portion of the first outer coil spring over which the first outer coil spring is free to bend or compress;
wherein the first inner coil spring has a second working length;
wherein the second working length is a length through which the first inner coil spring extends through turns along a free portion of the first inner coil spring over which the first inner coil spring is free to bend or compress;
wherein the first working length is substantially equal to the second working length;
a first anchor connected to a first end of the first dual spring member and configured to attach to a first lateral portion of a first vertebra of the spine;
a second anchor connected to a second end of the first dual spring member opposite to the first end of the first dual spring member and configured to attach to a first lateral portion of a second vertebra of the spine;
wherein a first end portion of the first outer coil spring is fixed to a first rod directly fixed to the first anchor and a second end portion of the first outer coil spring opposite to the first end portion of the first outer coil spring is fixed to a second rod directly fixed to the second anchor, the free portion of the first outer coil spring disposed between the first and second end portions of the first outer coil spring;
wherein a first end portion of the first inner coil spring is fixed to the first rod and a second end portion of the first inner coil spring opposite to the first end portion of the first inner coil spring is fixed to the second rod, the free portion of the first inner coil spring disposed between the first and second end portions of the first inner coil spring; and a second dynamic stabilization device comprising:
a second dual spring member including a second outer coil spring and a second inner coil spring inside the second outer coil spring;
wherein the second outer coil spring has a third working length;
wherein the third working length is a length through which the second outer coil spring extends through turns along a free portion of the second outer coil spring over which the second outer coil spring is free to bend or compress;
wherein the second inner coil spring has a fourth working length;
wherein the fourth working length is a length through which the second inner coil spring extends through turns along a free portion of the second inner coil spring over which the second inner coil spring is free to bend or compress;
wherein the third working length is substantially equal to the fourth working length;
a third anchor connected to a first end of the second dual spring member and configured to attach to a second lateral portion of the first vertebra of the spine, wherein the first and second lateral portions of the first vertebra are on opposite sides of a central spinous process portion of the first vertebra;
a fourth anchor connected to a second end of the second dual spring member opposite to the first end of the second dual spring member and configured to attach to a second lateral portion of the second vertebra of the spine, wherein the first and second lateral portions of the second vertebra are on opposite sides of a central spinous process portion of the second vertebra;
wherein a first end portion of the second outer coil spring is fixed to a third rod directly fixed to the third anchor and a second end portion of the second outer coil spring opposite to the first end portion of the second outer coil spring is fixed to a fourth rod directly fixed to the fourth anchor, the free portion of the second outer coil spring disposed between the first and second end portions of the second outer coil spring;
wherein a first end portion of the second inner coil spring is fixed to the third rod and a second end portion of the second inner coil spring opposite to the first end portion of the second inner coil spring is fixed to the fourth rod, the free portion of the second inner coil spring disposed between the first and second end portions of the second inner coil spring.

19. The dynamic stabilization system according to claim 18, wherein the first outer coil spring and the first inner coil spring of the first dynamic stabilization device are configured to provide residual tension, and wherein the second outer coil spring and the second inner coil spring of the second dynamic stabilization device are configured to provide residual compression.

20. The dynamic stabilization system according to claim 18, wherein the number of turns along the free portion of the first inner coil spring is greater than the number of turns along the free portion of the first outer coil spring, and wherein the number of turns along the free portion of the second inner coil spring is greater than the number of turns along the free portion of the second outer coil spring.

* * * * *